US009765153B2

(12) United States Patent
Brinkmann et al.

(10) Patent No.: US 9,765,153 B2
(45) Date of Patent: Sep. 19, 2017

(54) ANTI-BIOTIN ANTIBODIES AND METHODS OF USE

(71) Applicant: Hoffmann-La Roche Inc., Little Falls, NJ (US)

(72) Inventors: Ulrich Brinkmann, Weilheim (DE); Guy Georges, Habach (DE); Michael Grote, Penzberg (DE); Eike Hoffmann, Herrsching A. Ammersee (DE)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 110 days.

(21) Appl. No.: 14/576,916

(22) Filed: Dec. 19, 2014

(65) Prior Publication Data

US 2015/0232577 A1    Aug. 20, 2015

Related U.S. Application Data

(63) Continuation of application No. PCT/EP2013/064099, filed on Jul. 4, 2013.

(30) Foreign Application Priority Data

Jul. 4, 2012  (EP) .................................... 12174957

(51) Int. Cl.
*C07K 16/44* (2006.01)
*A61K 47/48* (2006.01)

(52) U.S. Cl.
CPC ........ *C07K 16/44* (2013.01); *A61K 47/48507* (2013.01); *C07K 2317/24* (2013.01); *C07K 2317/31* (2013.01); *C07K 2317/56* (2013.01)

(58) Field of Classification Search
CPC ................ C07K 16/44; C07K 2317/24; C07K 2317/31; C07K 2317/54; C07K 2317/56; C07K 2317/622; C07K 2317/624; C07K 2317/92; A61K 47/48507
See application file for complete search history.

(56) References Cited

U.S. PATENT DOCUMENTS

| | | | |
|---|---|---|---|
| 4,275,149 A | 6/1981 | Litman et al. |
| 4,318,980 A | 3/1982 | Boguslaski et al. |
| 4,524,025 A | 6/1985 | Geltosky |
| 4,676,980 A | 6/1987 | Segal et al. |
| 4,737,456 A | 4/1988 | Weng et al. |
| 4,816,567 A | 3/1989 | Cabilly et al. |
| 4,855,226 A | 8/1989 | Polito et al. |
| 4,855,522 A | 8/1989 | Diaz |
| 5,198,537 A | 3/1993 | Huber et al. |
| 5,208,020 A | 5/1993 | Chari et al. |
| 5,316,757 A | 5/1994 | Sherry et al. |
| 5,342,606 A | 8/1994 | Sherry et al. |
| 5,385,893 A | 1/1995 | Kiefer |
| 5,416,064 A | 5/1995 | Chari et al. |
| 5,428,139 A | 6/1995 | Kiefer et al. |
| 5,428,155 A | 6/1995 | Sherry et al. |
| 5,462,725 A | 10/1995 | Kiefer et al. |
| 5,480,990 A | 1/1996 | Kiefer et al. |
| 5,500,362 A | 3/1996 | Robinson et al. |
| 5,571,894 A | 11/1996 | Wels et al. |
| 5,587,458 A | 12/1996 | King et al. |
| 5,591,828 A | 1/1997 | Bosslet et al. |
| 5,624,821 A | 4/1997 | Winter et al. |
| 5,635,483 A | 6/1997 | Pettit et al. |
| 5,648,237 A | 7/1997 | Carter |
| 5,648,260 A | 7/1997 | Winter et al. |
| 5,712,374 A | 1/1998 | Kuntsmann et al. |
| 5,714,586 A | 2/1998 | Kunstmann et al. |
| 5,731,168 A | 3/1998 | Carter et al. |
| 5,739,116 A | 4/1998 | Hamann et al. |
| 5,739,294 A | 4/1998 | Kiefer et al. |
| 5,750,373 A | 5/1998 | Garrard et al. |
| 5,750,660 A | 5/1998 | Kiefer et al. |
| 5,767,285 A | 6/1998 | Hamann et al. |
| 5,770,429 A | 6/1998 | Lonberg et al. |
| 5,770,701 A | 6/1998 | McGahren et al. |
| 5,770,710 A | 6/1998 | McGahren et al. |
| 5,773,001 A | 6/1998 | Hamann et al. |
| 5,780,588 A | 7/1998 | Pettit et al. |
| 5,789,199 A | 8/1998 | Joly et al. |
| 5,804,371 A | 9/1998 | Hoss et al. |
| 5,821,337 A | 10/1998 | Carter et al. |
| 5,834,456 A | 11/1998 | Kiefer et al. |
| 5,840,523 A | 11/1998 | Simmons et al. |
| 5,869,046 A | 2/1999 | Presta et al. |
| 5,877,296 A | 3/1999 | Hamann et al. |
| 5,959,083 A | 9/1999 | Bosslet et al. |
| 5,959,177 A | 9/1999 | Hein et al. |
| 6,040,498 A | 3/2000 | Stomp et al. |
| 6,075,181 A | 6/2000 | Kucherlapati et al. |

(Continued)

FOREIGN PATENT DOCUMENTS

DE          3836656 A1      5/1990
EP        0 077 896 A1      5/1983
(Continued)

OTHER PUBLICATIONS

Rudikoff et al., Proc. Natl. Acad. Sci. USA 79: p. 1979-1983, 1982.*
Stancovski et al., Proceedings of the National Academy of Science USA 88: 8691-8695, 1991.*
Paul, Fundamental Immunology, (textbook), 1993, pp. 292-295.*
Wu et al., J. Mol. Biol. 294: 151-162, 1999.*
Riemer et al., Mol. Immunol. 42: 1121-1124, 2005.*
"AvantGen's Antibody Humanization and Discovery Technologies- Germliner$^{TM}$ Antibodies: An Effective and Proprietary Technology for Humanizing Antibodies Based on Epitope-Guided Selection", AvantGen, Inc. (Jul. 27, 2009).

(Continued)

*Primary Examiner* — Phuong Huynh

(74) *Attorney, Agent, or Firm* — Morrison & Foerster LLP

(57) ABSTRACT

The invention provides anti-biotin antibodies and methods of using the same.

20 Claims, 2 Drawing Sheets

(56) References Cited

U.S. PATENT DOCUMENTS

| | | |
|---|---|---|
| 6,150,584 A | 11/2000 | Kucherlapati et al. |
| 6,171,586 B1 | 1/2001 | Lam et al. |
| 6,194,551 B1 | 2/2001 | Idusogie et al. |
| 6,248,516 B1 | 6/2001 | Winter et al. |
| 6,267,958 B1 | 7/2001 | Andya et al. |
| 6,350,860 B1 | 2/2002 | Buyse et al. |
| 6,417,429 B1 | 7/2002 | Hein et al. |
| 6,420,548 B1 | 7/2002 | Vezina et al. |
| 6,511,663 B1 | 1/2003 | King et al. |
| 6,528,624 B1 | 3/2003 | Idusogie et al. |
| 6,602,684 B1 | 8/2003 | Umana et al. |
| 6,630,579 B2 | 10/2003 | Chari et al. |
| 6,737,056 B1 | 5/2004 | Presta |
| 6,881,536 B1 | 4/2005 | Shah et al. |
| 6,897,044 B1 | 5/2005 | Braslawsky et al. |
| 6,946,292 B2 | 9/2005 | Kanda et al. |
| 6,982,321 B2 | 1/2006 | Winter |
| 7,041,870 B2 | 5/2006 | Tomizuka et al. |
| 7,087,409 B2 | 8/2006 | Barbas, III et al. |
| 7,125,978 B1 | 10/2006 | Vezina et al. |
| 7,129,330 B1 | 10/2006 | Little et al. |
| 7,189,826 B2 | 3/2007 | Rodman |
| 7,332,581 B2 | 2/2008 | Presta |
| 7,371,826 B2 | 5/2008 | Presta |
| 7,498,298 B2 | 3/2009 | Doronina et al. |
| 7,504,256 B1 | 3/2009 | Ogawa et al. |
| 7,521,541 B2 | 4/2009 | Eigenbrot et al. |
| 7,527,791 B2 | 5/2009 | Adams et al. |
| 7,829,674 B2 | 11/2010 | Sabbadini et al. |
| 8,313,913 B2 | 11/2012 | Nakamura et al. |
| 8,945,867 B2 | 2/2015 | Ogawa et al. |
| 2001/0036923 A1 | 11/2001 | Chari et al. |
| 2002/0164328 A1 | 11/2002 | Shinkawa et al. |
| 2003/0115614 A1 | 6/2003 | Kanda et al. |
| 2003/0157108 A1 | 8/2003 | Presta |
| 2003/0166871 A1 | 9/2003 | Barbas, III et al. |
| 2004/0093621 A1 | 5/2004 | Shitara et al. |
| 2004/0109865 A1 | 6/2004 | Niwa et al. |
| 2004/0110282 A1 | 6/2004 | Kanda et al. |
| 2004/0110704 A1 | 6/2004 | Yamane et al. |
| 2004/0127688 A1 | 7/2004 | Winter |
| 2004/0132140 A1 | 7/2004 | Satoh et al. |
| 2005/0014934 A1 | 1/2005 | Hinton et al. |
| 2005/0026263 A1 | 2/2005 | Meares et al. |
| 2005/0031613 A1 | 2/2005 | Nakamura et al. |
| 2005/0059100 A1 | 3/2005 | Meares et al. |
| 2005/0079170 A1 | 4/2005 | Le Gall et al. |
| 2005/0079574 A1 | 4/2005 | Bond |
| 2005/0100543 A1 | 5/2005 | Hansen et al. |
| 2005/0119455 A1 | 6/2005 | Fuh et al. |
| 2005/0123546 A1 | 6/2005 | Umana et al. |
| 2005/0163782 A1 | 7/2005 | Glaser et al. |
| 2005/0233382 A1 | 10/2005 | Presta |
| 2005/0238649 A1 | 10/2005 | Doronina et al. |
| 2005/0260186 A1 | 11/2005 | Bookbinder et al. |
| 2005/0266000 A1 | 12/2005 | Bond et al. |
| 2005/0276802 A1 | 12/2005 | Adams et al. |
| 2005/0276805 A1 | 12/2005 | Hanai et al. |
| 2006/0025576 A1 | 2/2006 | Miller et al. |
| 2006/0104968 A1 | 5/2006 | Bookbinder et al. |
| 2006/0194291 A1 | 8/2006 | Presta |
| 2007/0061900 A1 | 3/2007 | Murphy et al. |
| 2007/0092940 A1 | 4/2007 | Eigenbrot et al. |
| 2007/0117126 A1 | 5/2007 | Sidhu et al. |
| 2007/0134759 A1 | 6/2007 | Nishiya et al. |
| 2007/0160598 A1 | 7/2007 | Dennis et al. |
| 2007/0166303 A1 | 7/2007 | Hanai et al. |
| 2007/0237764 A1 | 10/2007 | Birtalan et al. |
| 2007/0292936 A1 | 12/2007 | Barthelemy et al. |
| 2008/0069820 A1 | 3/2008 | Fuh et al. |
| 2008/0241884 A1 | 10/2008 | Shitara et al. |
| 2009/0002360 A1 | 1/2009 | Chen et al. |
| 2009/0093618 A1 | 4/2009 | Meares et al. |
| 2010/0111856 A1 | 5/2010 | Gill et al. |
| 2015/0166670 A1 | 6/2015 | Castoldi et al. |
| 2015/0238628 A1 | 8/2015 | Brinkmann et al. |
| 2015/0258209 A1 | 9/2015 | Benz et al. |
| 2017/0058050 A1 | 3/2017 | Brinkmann et al. |
| 2017/0058051 A1 | 3/2017 | Brinkmann et al. |

FOREIGN PATENT DOCUMENTS

| | | |
|---|---|---|
| EP | 0 098 179 A2 | 1/1984 |
| EP | 0 404 097 A2 | 12/1990 |
| EP | 0 425 235 A2 | 5/1991 |
| EP | 1 870 459 A1 | 12/2007 |
| JP | S58-046072 A | 3/1983 |
| JP | 2012-518892 A | 8/2012 |
| RU | 2219949 C2 | 12/2003 |
| RU | 2010108429 A | 9/2011 |
| WO | WO-91/06305 A1 | 5/1991 |
| WO | WO-92/04053 A1 | 3/1992 |
| WO | WO-93/01161 A1 | 1/1993 |
| WO | WO-93/08829 A1 | 5/1993 |
| WO | WO-93/16185 A2 | 8/1993 |
| WO | WO-93/16185 A3 | 8/1993 |
| WO | WO-93/21232 A1 | 10/1993 |
| WO | WO-94/11026 A2 | 5/1994 |
| WO | WO-94/11026 A3 | 5/1994 |
| WO | WO-94/29351 A2 | 12/1994 |
| WO | WO-94/29351 A3 | 12/1994 |
| WO | WO-95/09917 A1 | 4/1995 |
| WO | WO-96/027011 A1 | 9/1996 |
| WO | WO-97/01580 A1 | 1/1997 |
| WO | WO-97/25069 A1 | 7/1997 |
| WO | WO-97/30087 A1 | 8/1997 |
| WO | WO-98/50431 A2 | 11/1998 |
| WO | WO-98/50431 A3 | 11/1998 |
| WO | WO-98/58964 A1 | 12/1998 |
| WO | WO-99/22764 A1 | 5/1999 |
| WO | WO-99/51642 A1 | 10/1999 |
| WO | 00/50088 A2 | 8/2000 |
| WO | WO-00/61739 A1 | 10/2000 |
| WO | WO-01/29246 A1 | 4/2001 |
| WO | WO-01/77342 A1 | 10/2001 |
| WO | WO-02/31140 A1 | 4/2002 |
| WO | WO-03/011878 A2 | 2/2003 |
| WO | WO-03/011878 A3 | 2/2003 |
| WO | WO-03/084570 A1 | 10/2003 |
| WO | WO-03/085107 A1 | 10/2003 |
| WO | WO-03/085119 A1 | 10/2003 |
| WO | WO-03/084570 A1 | 12/2003 |
| WO | WO-2004/045642 A1 | 6/2004 |
| WO | WO-2004/056312 A2 | 7/2004 |
| WO | WO-2004/056312 A3 | 7/2004 |
| WO | WO-2004/065569 A2 | 8/2004 |
| WO | WO-2004/065569 A3 | 8/2004 |
| WO | WO-2005/004809 A2 | 1/2005 |
| WO | WO-2005/035586 A1 | 4/2005 |
| WO | WO-2005/035778 A1 | 4/2005 |
| WO | WO-2005/053742 A1 | 6/2005 |
| WO | WO-2005/100402 A1 | 10/2005 |
| WO | WO-2006/020258 A2 | 2/2006 |
| WO | WO-2006/020258 A3 | 3/2006 |
| WO | WO-2006/029879 A2 | 3/2006 |
| WO | WO-2006/029879 A3 | 3/2006 |
| WO | WO-2006/044908 A2 | 4/2006 |
| WO | WO-2006/044908 A3 | 4/2006 |
| WO | WO-2007/024715 A2 | 3/2007 |
| WO | WO-2007/024715 A3 | 3/2007 |
| WO | WO-2007/065808 A2 | 6/2007 |
| WO | WO-2007/065808 A3 | 6/2007 |
| WO | WO-2007/109254 A2 | 9/2007 |
| WO | WO-2007/109254 A3 | 9/2007 |
| WO | WO-2008/077546 A1 | 7/2008 |
| WO | WO-2009/022328 A2 | 2/2009 |
| WO | WO-2009/080251 A1 | 7/2009 |
| WO | WO-2009/080252 A1 | 7/2009 |
| WO | WO-2009/080253 A1 | 7/2009 |
| WO | WO-2009/080254 A1 | 7/2009 |
| WO | WO-2009/089004 A1 | 7/2009 |
| WO | 2010/034651 A1 | 4/2010 |
| WO | WO-2010/045388 A2 | 4/2010 |
| WO | WO-2010/045388 A3 | 4/2010 |

(56) References Cited

FOREIGN PATENT DOCUMENTS

| | | |
|---|---|---|
| WO | WO-2010/056893 A1 | 5/2010 |
| WO | WO-2010/098992 A1 | 9/2010 |
| WO | WO-2010/112193 A1 | 10/2010 |
| WO | WO-2010/115589 A1 | 10/2010 |
| WO | WO-2010/119704 A1 | 10/2010 |
| WO | WO-2010/136172 A1 | 12/2010 |
| WO | WO-2010/145792 A1 | 12/2010 |
| WO | WO-2010/145793 A1 | 12/2010 |
| WO | WO-2011/003557 A1 | 1/2011 |
| WO | WO-2011/003780 A1 | 1/2011 |
| WO | WO-2011/032022 A1 | 3/2011 |
| WO | WO-2012/093068 A1 | 7/2012 |
| WO | WO-2014/006124 A1 | 1/2014 |
| WO | WO-2015/101587 A1 | 7/2015 |
| WO | WO-2015/101589 A1 | 7/2015 |

OTHER PUBLICATIONS

Hwang et al. "Use of Human Germline Genes in a CDR Homology-based Approach to Antibody Humanization," *Methods* 36(1):35-42, (May 2005).
Almagro et al. (2008). "Humanization of antibodies," Front. Biosci. 13:1619-1633.
Baca et al. (1997). "Antibody humanization using monovalent phage display," J. Biol. Chem. 272:10678-10684.
Brennan et al. (1985). "Preparation of bispecific antibodies by chemical recombination of monoclonal immunoglobulin G1 fragments," Science 229:81-83.
Bruggemann et al. (1987). "Comparison of the effector functions of human immunoglobulins using a matched set of chimeric antibodies," J. Exp. Med. 166:1351-1361.
Carter et al. (1992). "Humanization of an anti-p185HER2 antibody for human cancer therapy," PNAS 89:4285-4289.
Chari, R.V., et al. (1992). "Immunoconjugates containing novel maytansinoids: promising anticancer drugs," Cancer Res. 52:127-131.
Charlton, K.A., In: Methods in Molecular Biology, vol. 248, Lo, B.K.C. (ed.), Humana Press, Totowa, NJ (2003), pp. 245-254.
Chen et al. (1999). "Selection and analysis of an optimized anti-VEGF antibody: crystal structure of an affinity-matured Fab in complex with antigen," J. Mol. Biol. 293:865-881.
Chothia et al. (1987). "Canonical structures for the hypervariable regions of immunoglobulins," J. Mol. Biol. 196:901-917.
Chowdhury, P.S. (2003). "Engineering hot spots for affinity enhancement of antibodies," Methods Mol. Biol. 207:179-196.
Clackson et al. (1991). "Making antibody fragments using phage display libraries," Nature 352:624-628.
Clynes, R., et al. (1998). "Fc receptors are required in passive and active immunity to melanoma" Proc. Natl. Acad. Sci. USA 95:652-656.
Collaborative Computational Project, No. 4 (1994). "The CCP4 suite: programs for protein crystallography," Acta Crystallogr. Section D. 50(Pt. 5):760-763.
Cragg, M.S., et al. (2003). "Complement-mediated lysis by anti-CD20 mAb correlates with segregation into lipid rafts," Blood 101:1045-1052.
Cragg et al. (2004). "Antibody specificity controls in vivo effector mechanisms of anti-CD20 reagents," Blood 103:2738-2743.
Cunningham et al. (1989). "High-resolution epitope mapping of hGH-receptor interactions by alanine-scanning mutagenesis," Science 244:1081-1085.
Dall'Acqua et al. (2005). "Antibody humanization by framework shuffling," Methods 36:43-60.
Dubowchik et al. (2002). "Doxorubicin immunoconjugates containing bivalent, lysosomally-cleavable dipeptide linkages," Bioorg. & Med. Chem. Letters 12:1529-1532.
Duncan et al. (1988). "The binding site for C1q on IgG," Nature 332:738-740.

Emsley, P., et al. (2010). "Features and development of Coot," Acta Crystallogr. D Biol. Crystallogr. 66:486-501.
Flatman et al. (2007). "Process analytics for purification of monoclonal antibodies," J. Chrom. B. 848:79-87.
Gazzano-Santoro et al. (1997). "A non-radioactive complement-dependent cytotoxicity assay for anti-CD20 monoclonal antibody," J. Immunol. Methods 202:163-171.
Gerngross, T.U. (2004). "Advances in the production of human therapeutic proteins in yeasts and filamentous fungi," Nat. Biotech. 22:1409-1414.
Graham, F.L., et al. (1977). "Characteristics of a human cell line transformed by DNA from human adenovirus type 5," J. Gen Virol. 36:59-74.
Gruber et al. (1994). "Efficient tumor cell lysis mediated by a bispecific single chain antibody expressed in *Escherichia coli*," J. Immunol. 152:5368-5374.
Guyer, R.L., et al. (1976). "Immunoglobulin binding by mouse intestinal epithelial cell receptors," J. Immunol. 117 (1976) 587-593.
Hellstrom et al. (1986). "Antitumor effects of L6, an IgG2a antibody that reacts with most human carcinomas," PNAS 83:7059-7063.
Hellstrom et al. (1985). "Strong antitumor activities of IgG3 antibodies to a human melanoma-associated ganglioside," PNAS 82:1499-1502.
Hinman, L.M., et al. (1993). "Preparation and characterization of monoclonal antibody conjugates of the calicheamicins: a novel and potent family of antitumor antibiotics," Cancer Res. 53:3336-3342.
Holliger, P., et al. (1993). "Diabodies: small bivalent and bispecific antibody fragments," Proc. Natl. Acad. Sci. USA 90:6444-6448.
Hoogenboom, H.R., et al. (2002). "Overview of antibody phage-display technology and its applications," Methods in Molecular Biology 178:1-37.
Hudson et al. (2003). "Engineered antibodies," Nat. Med. 9:129-134.
Idusogie et al. (2000). "Mapping of the C1q binding site on rituxan, a chimeric antibody with a human IgG1 Fc," J. Immunol. 164:4178-4184.
International Search Report mailed on Aug. 20, 2013, for PCT Patent Application No. PCT/EP2013/064099, filed on Jul. 4, 2013, six pages.
Jeffrey, S.C., et al. (2006). "Dipeptide-based highly potent doxorubicin antibody conjugates," Bioorg. Med. Chem. Lett. 16:358-362.
Kabsch, W.. (1993). "Automatic processing of rotation diffraction data from crystals of initially unknown symmetry and cell constants," J. Appl. Cryst. 26:795-800.
Kam, N.W., et al. (2005). "Carbon nanotubes as multifunctional biological transporters and near-infrared agents for selective cancer cell destruction," PNAS 102:11600-11605.
Kanda, Y., et al. (2006). "Comparison of cell lines for stable production of fucose-negative antibodies with enhanced ADCC," Biotechnol. Bioeng. 94:680-688.
Kashmiri et al. (2005). "SDR grafting—a new approach to antibody humanization" Methods 36:25-34.
Kim, J.K., et al. (1994). "Localization of the site of the murine IgG1 molecule that is involved in binding to the murine intestinal Fc receptor," J. Immunol. 24:2429-2434.
Kindt, T.J., et al., Kuby Immunology, 6th ed., W.H. Freeman and Co., N.Y. (2007), p. 91.
King, H.D., et al. (2002). "Monoclonal antibody conjugates of doxorubicin prepared with branched peptide linkers: inhibition of aggregation by methoxytriethyleneglycol chains," J. Med. Chem. 45:4336-4343.
Klimka (2000). "Human anti-CD30 recombinant antibodies by guided phage antibody selection using cell panning," Br. J. Cancer 83:252-260.
Kostelny et al. (1992). "Formation of a bispecific antibody by the use of leucine zippers," J. Immunol. 148:1547-1553.
Kratz, F., et al. (2006). "Prodrugs of anthracyclines in cancer chemotherapy," Curr. Med. Chem. 13:477-523.
Laskowski (1993). "PROCHECK: a program to check the stereochemical quality of protein structures," J. Appl. Crystallogr. 26, 283-291.

(56) References Cited

OTHER PUBLICATIONS

Li, H., et al. (2006). "Optimization of humanized IgGs in glycoengineered Pichia pastoris," Nat. Biotech. 24:210-215.
Lode, H.N., et al. (1998). "Targeted therapy with a novel enediyene antibiotic calicheamicin theta(I)1 effectively suppresses growth and dissemination of liver metastases in a syngeneic model of murine neuroblastoma," Cancer Res. 58:2925-2928.
Mather, J.P. (1980). "Establishment and characterization of two distinct mouse testicular epithelial cell lines," Biol. Reprod. 23:243-252.
Mather, J.P., et al. (1982). "Culture of testicular cells in hormone-supplemented serum-free medium," Annals N.Y. Acad. Sci. 383:44-68.
Milstein (1983). "Hybrid hybridomas and their use in immunohistochemistry," Nature 305:537-540.
Morrison et al. (1984). "Chimeric human antibody molecules: mouse antigen-binding domains with human constant region domains," PNAS 81:6851-6855.
Murshudov, G.N., et al. (1997). "Refinement of macromolecular structures by the maximum-likelihood method" Acta Crystallogr. D Biol. Crystallogr. 53:240-255.
Nagy, A., et al. (2000). "Stability of cytotoxic luteinizing hormone-releasing hormone conjugate (AN-152) containing doxorubicin 14-O-hemiglutarate in mouse and human serum in vitro: implications for the design of preclinical studies," PNAS 97:829-834.
Neuberger, M.S. (1983). "Expression and regulation of immunoglobulin heavy chain gene transfected into lymphoid cells," EMBO J. 2:1373-1378.
Okazaki, A., et al. (2004). "Fucose depletion from human IgG1 oligosaccharide enhances binding enthalpy and association rate between IgG1 and FcgammaRIIIa," J. Mol. Biol. 336:1239-1249.
Osbourn et al. (2005). "From rodent reagents to human therapeutics using antibody guided selection," Methods 36:61-68.
Pace, et al. (1995). "How to measure and predict the molar absorption coefficient of a protein," Protein Science 4:2411-2423.
Padlan et al. (1991). "A possible procedure for reducing the immunogenicity of antibody variable domains while preserving their ligand-binding properties," Mol. Immunol. 28:489-498.
Petkova, S.B., et al. (2006). "Enhanced half-life of genetically engineered human IgG1 antibodies in a humanized FcRn mouse model: potential application in humorally mediated autoimmune disease," Int. Immunol. 18:1759-1769.
Pluckthun, A., In: The Pharmacology of Monoclonal Antibodies, vol. 113, Rosenburg and Moore (eds.), Springer-Verlag, New York (1994), pp. 269-315.
Portolano et al. (1993). "Lack of promiscuity in autoantigen-specific H and L chain combinations as revealed by human H and L chain roulette," J. Immunol. 150:880-887.
Presta et al. (1993). "Humanization of an antibody directed against IgE" J. Immunol. 151:2623-2632.
Presta et al. (1997). "Humanization of an anti-vascular endothelial growth factor monoclonal antibody for the therapy of solid tumors and other disorders," Cancer Res. 57:4593-4599.
Queen et al. (1989). "A humanized antibody that binds to the interleukin 2 receptor" PNAS 86:10029-10033.
Ravetch et al. (1991). "Fc receptors," Annu. Rev. Immunol. 9:457-492.
Reiter, Y., et al. (1996). "Engineering antibody Fv fragments for cancer detection and therapy: disulfide-stabilized Fv fragments," Nature biotechnology 14 (1996) 1239-1245.
Riechmann et al. (1988). "Reshaping human antibodies for therapy," Nature 332:323-329.
Ripka, J., et al. (1986). "Two Chinese hamster ovary glycosylation mutants affected in the conversion of GDP-mannose to GDP-fucose," Arch. Biochem. Biophys. 249:533-545.
Rosok et al. (1996). "A combinatorial library strategy for the rapid humanization of anticarcinoma BR96 Fab" J. Biol. Chem. 271:22611-22618.

Shields, R.L., et al. (2001). "High resolution mapping of the binding site on human IgG1 for Fc γ RI, Fc γ RII, Fc γ RIII, and FcRn and design of IgG1 variants with improved binding to the Fc γ R," J. Biol. Chem. 276:6591-6604.
Sims et al. (1993). "A humanized CD18 antibody can block function without cell destruction," J. Immunol. 151:2296-2308.
Torgov, M.Y., et al. (2005). "Generation of an intensely potent anthracycline by a monoclonal antibody-beta-galactosidase conjugate," Bioconjug. Chem. 16:717-721.
Traunecker et al. (1991). "Bispecific single chain molecules (Janusins) target cytotoxic lymphocytes on HIV infected cells," EMBO J. 10:3655-3659.
Tutt et al. (1991). "Trispecific F(ab')3 derivatives that use cooperative signaling via the TCR/CD3 complex and CD2 to activate and redirect resting cytotoxic T cells," J. Immunol. 147:60-69.
Urlaub, G., et al. (1980). "Isolation of Chinese hamster cell mutants deficient in dihydrofolate reductase activity," PNAS 77:4216-4220.
Vitetta, E.S., et al. (1987). "Redesigning nature's poisons to create anti-tumor reagents," Science 238:1098-1104.
Wright et al. (1997). "Effect of glycosylation on antibody function: implications for genetic engineering," Trends Biotech. 15:26-32.
Written Opinion of the International Searching Authority mailed on Aug. 20, 2013, for PCT Patent Application No. PCT/EP2013/064099, filed on Jul. 4, 2013, eight pages.
Yamane-Ohnuki, N., et al. (2004). "Establishment of FUT8 knock-out Chinese hamster ovary cells: an ideal host cell line for producing completely defucosylated antibodies with enhanced antibody-dependent cellular cytotoxicity," Biotech. Bioeng. 87:614-622.
Yazaki, P. and Wu, A.M., Methods in Molecular Biology, vol. 248, Lo, B.K.C. (ed.), Humana Press, Totowa, NJ (2004), pp. 255-268.
U.S. Appl. No. 14/551,957, filed Nov. 24, 2014, by Castoldi et al.
U.S. Appl. No. 14/576,033, filed Dec. 18, 2014, by Brinkmann et al.
U.S. Appl. No. 14/577,084, filed Dec. 19, 2014, by Benz et al.
Bagci et al., "Monoclonal Anti-Biotin Antibodies Simulate Avidin in the Recognition of Biotin" FEBS Letter 322(1):47-50 ( 1993).
Berger, "Production of Antibodies that Bind Biotin and Inhibit Biotin Containing Enzymes" Biochemistry 14(11):2338-2342 ( 1975).
Cao et al., "Development of Bispecific Monoclonal Antibody as a Universal Immunoprobe for Detecting Biotinylated Macromolecules" Journal of Immunological Methods 220:85-91 ( 1998).
Chowdhury, "Targeting Random Mutations to Hotspots in Antibody Variable Domains for Affinity Improvement" Methods in Molecular Biology 178:269-285 ( 2001).
Dakshinamurti et al., "production and Characterization of a Monoclonal Antibody to Biotin" Biochemical Journal 237:477-482 ( 1986).
Kohen et al., "Preparation and Properties of Anti-Biotin Antibodies" Methods in Enzymology :279:451-463 ( 1997).
Vincent et al., "A Comparison of the Binding of Biotin and Biotinylated Macromolecular Ligands to an Anti-Biotin Monoclonal Antibody and to Streptavidin" Journal of Immunological Methods 165:177-182 ( 1993).
Wark et al., "Latest Technologies for the Enhancement of Antibody Affinity" Advanced Drug Delivery Reviews 58:657-670 ( 2006).
Wu, "Simultaneous Humanization and Affinity Optimization of Monoclonal Antibodies" Methods in Molecular Biology 207:197-212 ( 2003).
Albert et al. "Direct Synthesis of [DOTA-DPhe1]-Octreotide and [DOTA-DPhe1, Tyr3]-Octreotide (SMT487): Two Conjugates for Systemic Delivery of Radiotherapeutical Nuclides to Somatostatin Receptor Positive Tumors in Man," *Bioorganic & Medicinal Chemistry Letters* 8:1207-1210, (1998).
Atwell et al. "Stable Heterodimers from Remodeling the Domain Interface of a Homodimer Using a Phage Display Library," *J. Mol. Biol.* 270:26-35, (1997).
Bera et al. "Comparison of Recombinant Immunotoxins Against Le$^Y$ Antigen Expressing Tumor Cells: Influence of Affinity, Size, and Stability," *Bioconjugate Chemistry* 9(6):736-743, (Nov.-Dec. 1998; e-published on Oct. 20, 2008).
Blend et al. "Labeling anti-HER2/neu Monoclonal Antibodies With $^{111}$In and $^{90}$Y Using a Bifunctional DTPA Chelating Agent," *Cancer Biotherapy & Radiopharmaceuticals* 18(3):355-363, (2003).

(56) References Cited

OTHER PUBLICATIONS

Boerner et al. "Production of Antigen-Specific Human Monoclonal Antibodies from in Vitro-Primed Human Splenocytes," *The Journal of Immunology* 147(1):86-95, (Jul. 1, 1991).
Briggs et al. "Synthesis of Functionalised Fluorescent Dyes and Their Coupling to Amines and Amino Acids," *J. Chem. Soc., Perkin-Trans.* 1:1051-1058, (1997).
Brinkley. "A Brief Survey of Methods for Preparing Protein Conjugates with Dyes, Haptens and Crosslinking Reagents," *Bioconjugate Chem.* 3(1):2-13, (Jan. 1992).
Brodeur et al. "Mouse-Human Myeloma Partners for the Production of Heterohybridomas," in Chapter 4 of *Monoclonal Antibody Production Techniques and Applications*, Marcel Dekker, Inc., New York, pp. 51-63, (1987).
Cahn et al. "Specification of Molecular Chirality," *Angew. Chem. Int. Ed. Engl.* 5(4):385-415, (1966).
Camera et al. "Comparative Biodistribution of Indium- and Yttrium-Labeled B3 Monoclonal Antibody Conjugated to Either 2-(p-SCN-Bz)-6-Methyl-DTPA (1 B4M-DTPA) or 2-(p-SCN-Bz)-1,4,7,10-Tetraazacyclododecane Tetraacetic Acid (2B-DOTA)," *European Journal of Nuclear Medicine* 21(7):640-646, (Jul. 1994).
Camera et al. "Evaluation of a New DTPA-Derivative Chelator: Comparative Biodistribution and Imaging Studies of *111*In-Labeled B3 Monoclonal Antibody in Athymic Mice Bearing Human Epidermoid Carcinoma Xenografts," *Nucl. Med. Biol.* 20(8):955-962, (1993).
Chen et al. "MicroPET and Autoradiographic Imaging of Breast Cancer $\alpha_v$-Integrin Expression Using $^{18}$F- And $^{64}$Cu-Labeled RGD Peptide," *Bioconjugate Chem.* 15(1):41-49, (2004, e-published on Dec. 30, 2003).
Coloma et al. "Design and Production of Novel Tetravalent Bispecific Antibodies" *Nature Biotech* 15(2):159-163, (Feb. 1997).
De León-Rodriguez et al. "Solid-Phase Synthesis of DOTA-Peptides," *Chem. Eur. J.* 10:1149-1155, (2004).
Debinski et al. "An Immunotoxin with Increased Activity and Homogeneity Produced by Reducing the Number of Lysine Residues in Recombinant Pseudomonas Exotoxin," *Bioconjugate Chem.* 5(1):40-46, (Jan. 1994).
Debinski et al. "Monovalent Immunotoxin Containing Truncated Form of Pseudomonas Exotoxin as Potent Antitumor Agent," *Cancer Research* 52(19):5379-5385, (Oct. 1, 1992).
Decarie et al. "Development of Digoxigenin-Labeled Peptide: Application to Chemiluminoenzyme Immunoassay of Bradykinin in Inflamed Tissues," *Peptides* 15(3):511-518, (1994).
Denardo et al. "Comparison of 1,4,7,10-Tetraazacyclododecane-N,N'N"N"'-Tetraacetic Acid (DOTA)-Peptide-ChL6, a Novel Immunoconjugate with Catabolizable Linker, to 2-Iminothiolane-2[p-(Bromoacetamido)benzyl]-DOTA-ChL6 in Breast Cancer Xenografts," *Clinical Cancer Research* 4(10):2483-2490, (Oct. 1, 1998).
Dengl et al. "Hapten-Directed Spontaneous Disulfide Shuffling: A Universal Technology for Site-Directed Covalent Coupling of Payloads to Antibodies," *FASEB J* 29(5):1763-1779, (May 2015; e-published on Feb. 10, 2015).
Dermer. "Another Anniversary for the War on Cancer," *Nature Bio/Technology* 12:320, (Mar. 1994).
Doppalapudi et al. "Chemical Generation of Bispecific Antibodies," *PNAS* 107(52):22611-22616, (Dec. 28, 2010).
Fellouse et al. "Synthetic Antibodies from a Four-Amino-Acid Code: A Dominant Role for Tyrosine in Antigen Recognition," *PNAS* 101(34):12467-12472, (Aug. 24, 2004).
Fischer et al. "Bispecific Antibodies: Molecules that Enable Novel Therapeutic Strategies," *Pathobiology* 74:3-14, (2007).
Fraker et al "Protein and Cell Membrane Iodinations with a Sparingly Soluble Chloroamide, 1, 3, 4, 6-Tetrachloro-3a, 6a-Diphenylglycoluril," *Biochem. Biophys. Res. Commun.* 80(4):849-857, (Feb. 28, 1978).
Griffiths et al. "Human Anti-Self Antibodies with High Specificity from Phage Display Libraries," *The EMBO Journal* 12(2):725-734, (1993).

Hanes et al. "Ribosome Display Efficiently Selects and Evolves High-Affinity Antibodies in Vitro From Immune Libraries," *Proceedings of the National Academy of Sciences* 95(24):14130-14135, (Nov. 24, 1998).
Hansen et al. "A Recombinant Immunotoxin Targeting CD22 With Low Immunogenicity, Low Nonspecific Toxicity, and High Antitumor Activity in Mice," *Journal of Immunotherapy* 33(3):297-304, (Apr. 2010).
Hermanson. "Functional Targets," in Chapter 1 of *Bioconjugate Techniques*, Academic Press, San Diego, pp. 3-168, (1996).
Hermanson. "Buckyballs, Fullerenes, and Carbon Nanotubes," in Chapter 15 of *Bioconjugate Techniques*, Academic Press, San Diego, pp. 627-648, (1996).
Hermanson. "Chemoselective Ligation: Bioorthogonal Reagents" in Chapter 17 of *Bioconjugate Techniques*, Academic Press, San Diego, pp. 666-706, (1996).
Hermanson. "Mass Tags and Isotope Tags," in Chapter 16 of *Bioconjugate Techniques*, Academic Press, San Diego, pp. 649-665, (1996).
Hnatowich et al. "The Preparation of DTPA-Coupled Antibodies Radiolabeled With Metallic Radionuclides: An Improved Method," *Journal of Immunological Methods* 65:147-157, (1983).
Hoffmann et al. "PK Modulation of Haptenylated Peptides Via Non-Covalent Antibody Complexation," *Journal of Controlled Release* 171(1):48-56, (Oct. 10, 2013, e-published on Jun. 22, 2013).
Holliger et al. "Engineered Antibody Fragments and the Rise of Single Domains," *Nature Biotech* 23(9):1126-1136, (Sep. 2005; e-published on Sep. 7, 2005).
Hoogenboom et al. "By-Passing Immunisation. Human Antibodies from Synthetic Repertoires of Germline $V_H$ Gene Segments Rearranged in Vitro," *J. Mol. Biol.* 227:381-388, (1992).
Izard et al. "An Improved Method for Labeling Monoclonal Antibodies With Samarium-153: Use of the Bifunctional Chelate 2-(p-Isothiocyanatobenzyl)-6-Methyldiethylenetriaminepentaacetic Acid," *Bioconjugate Chem.* 3(4):346-350, (1992).
Klussman et al. "Secondary mAb—vcMMAE Conjugates are Highly Sensitive Reporters of Antibody Internalization Via the Lysosome Pathway," *Bioconjugate Chemistry* 15(4):765-773, (2004, e-published on Jun. 18, 2004).
Kobayashi et al. "Evaluation of the in Vivo Biodistribution of Indium-111 and Yttrium-88 Labeled Dendrimer-1B4M-DTPA and Its Conjugation With Anti-Tac Monoclonal Antibody," *Bioconjugate Chem.* 10:103-111, (1999, e-published on Dec. 10, 1998).
Kobayashi et al. "Evaluation of the in Vivo Biodistribution of Yttrium-Labeled Isomers of CHX-DTPA-Conjugated Monoclonal Antibodies," *J. Nucl. Med.* 39:829-836, (1998).
Kozbor. "A Human Hybrid Myeloma for Production of Human Monoclonal Antibodies," *The Journal of Immunology* 133(6):3001-3005, (Dec. 1984).
Kukis et al. "Optimized Conditions for Chelation of Yttrium-90-Dota Immunoconjugates," *The Journal of Nuclear Medicine* 39(12):2105-2110, (Dec. 1998).
Lee et al. "High Affinity Human Antibodies from Phage Displayed Synthetic Fab Libraries with a Single Framework Scaffold," *J. Mol. Biol.* 340:1073-1093, (2004).
Lee et al. "Specific Localization, Gamma Camera Imaging, and Intracellular Trafficking of Radiolabelled Chimeric Anti-G(d3) Ganglioside Monoclonal Antibody KM871 in SK-MEL-28 Melanoma Xenografts," *Cancer Research* 61(1 1):4474-4482, (Jun. 1, 2001).
Lee et al., "Bivalent Antibody Phage Display Mimics Natural Immunoglobulin," *Journal of Immunological Methods* 284:119-132, (2004).
Lewis et al. "An Improved Method for Conjugating Monoclonal Antibodies with N-Hydroxysulfosuccinimidyl DOTA" *Bioconjugate Chem.* 12(2):320-324, (2001).
Li et al. "Human Antibodies for Immunotherapy Development Generated Via a Human B Cell Hybridoma Technology," *PNAS* 103(10):3557-3562, (Mar. 7, 2006).
Li et al. "Vinyl Sulfone Bifunctional Derivatives of DOTA Allow Sulfhydryl- or Amino-Directed Coupling to Antibodies. Conjugates

(56) References Cited

OTHER PUBLICATIONS

Retain Immunoreactivity and Have Similar Biodistributions," *Bioconjugate Chem.* 13:110-115, (2002, e-published on Dec. 14, 2001).
Lonberg. "Fully Human Antibodies from Transgenic Mouse and Phage Display Platforms," *Curr. Opin. Immunol.* 20:450-459, (2008; e-published on Jul. 21, 2008).
Lonberg. "Human Antibodies from Transgenic Animals," *Nature Biotechnology* 23(9):1117- 1125, (Sep. 2005; e-published on Sep. 7, 2005).
MacCallum et al. "Antibody-antigen Interactions: Contact Analysis and Binding Site Topography," *J. Mol. Biol.* 262:732-745, (1996).
Manheimer-Lory et al. "Lupus-specific Antibodies Reveal an Altered Pattern of Somatic Mutation," *J. Clin. Invest.* 100(10):2538-2546, (Nov. 1997).
Mardirossian et al. "The Stability in Liver Homogenates of Indium-111 and Yttrium-90 Attached to Antibody Via Two Popular Chelators," *Nucl. Med. Biol.* 20(1):65-74, (1993).
Marks et al. "By-Passing Immunization. Human Antibodies from V-Gene Libraries Displayed on Phage," *J. Mol. Biol.* 222:581-597, (1991).
Marks et al. "Selection of Human Antibodies from Phage Display Libraries," Chapter 8 in *Methods in Molecular Biology*, LO, B.K.C. (ed.), Humana Press Inc., Totowa, NJ, 248:161-176, (2004), twenty nine pages.
McCafferty et al. "Phage Antibodies: Filamentous Phage Displaying Antibody Variable Domains," *Nature* 348:552-554, (Dec. 6, 1990).
Meares et al. "Macrocyclic Chelates of Radiometals for Diagnosis and Therapy," *Br. J. Cancer Suppl.* X:21-26, (1990).
Meares et al. "Conjugation of Antibodies With Bifunctional Chelating Agents: Isothiocyanate and Bromoacetamide Reagents, Methods of Analysis, and Subsequent Addition of Metal Ions," *Analytical Biochemistry* 142:68-78, (1984).
Merchant et al. "An Efficient Route to Human Bispecific IgG," *Nature Biotechnology* 16:677- 681, (Jul. 1998).
Metz et al. "Bispecific Digoxigenin-binding Antibodies for Targeted Payload Delivery," *PNAS* 108(20):8194-8199, (May 17, 2011).
Miederer et al. "Pharmacokinetics, Dosimetry, and Toxicity of the Targetable Atomic Generator, $^{225}$Ac-HuM195, in Nonhuman Primates," *The Journal of Nuclear Medicine* 45(1):129-137, (Jan. 2004).
Mier et al. "Conjugation of DOTA Using Isolated Phenolic Active Esters: The Labeling and Biodistribution of Albumin as Blood Pool Marker," *Bioconjugate Chem.* 16(1):237-240, (2005; e-published on Dec. 7, 2004).
Mirzadeh et al. "Radiometal Labeling of Immunoproteins: Covalent Linkage of 2-(4-Isothiocyanatobenzyl)Diethylenetriaminepentaacetic Acid Ligands to Immunoglobulin," *Bioconjugate Chem.* 1(1):59-65, (1990).
Mitchell et al. "Targeting Primary Human Ph$^+$ B-cell Precursor Leukemia-engrafted SCID Mice Using Radiolabeled Anti-CD19 Monoclonal Antibodies," *The Journal of Nuclear Medicine* 44(7)1105-1112, (Jul. 2003).
Morrison. "Two Heads are Better Than One," *Nature Biotechnology* 25(11):1233-1234, (Nov. 2007).
Nguyen et al. "Camel Heavy-chain Antibodies: Diverse Germline $V_hH$ and Specific Mechanisms Enlarge the Antigen-binding Repertoire," *The EMBO Journal* 19(5):921-930, (2000).
Ni."Research Progress and Future Perspectives in Antibodomics and Antibodomic Drugs," *Xiandai Mianyixue* 26(4):265-268, (2006), (with English Translation).
Nikula et al. "A Rapid, Single Vessel Method for Preparation of Clinical Grade Ligand Conjugated Monoclonal Antibodies," *Nucl. Med. Biol.* 22(3):387-390, (1995).
Nikula et al. "Alpha-Emitting Bismuth Cyclohexylbenzyl DTPA Constructs of Recombinant Humanized Anti-CD33 Antibodies: Pharmacokinetics, Bioactivity, Toxicity and Chemistry," *The Journal of Nuclear Medicine* 40(1):166-176, (Jan. 1999).

Nygaard et al. "The PP-Fold Solution Structure of Human Polypeptide YY and Human PYY3-36 As Determined by NMR," *Biochemistry* 45(27):8350-8357, (Jun. 16, 2006).
Ohno et al. "Antigen-binding Specificities of Antibodies are Primarily Determined by Seven Residues of $V_H$," *Proc. Natl. Acad. Sci. USA* 82(9):2945-2949, (May 1985).
O'Sullivan et al. "Methods for the Preparation of Enzyme-Antibody Conjugates for use in Enzyme Immunoassay," in Chapter 9 of *Methods in Enzymology* (ed. By J. Langone & IT Van Vunakis), Academic Press, New York, 73:147-166, (1981).
Pai et al. "Anti-tumor Activities of Immunotoxins Made of Monoclonal Antibody B3 and Various Forms of Pseudomonas Exotoxin," *Proceedings of the National Academy of Sciences, USA* 88(8):3358-3362, (Apr. 15, 1991).
Pastan et al. "Immunotoxins with Decreased Immunogenicity and Improved Activity," *Leukemia & Lymphoma* 52(Supp. 2):87-90, (Jun. 2011; e-published on Apr. 19, 2011).
Picard. "A Lymphocyte-specific Enhancer in the Mouse Immunoglobulin κ Gene," *Nature* 307:80-82, (Jan. 5, 1984).
Polya. *Biochemical Targets of Plant Bioactive Compounds*, Taylor & Francis Inc., 29 West 35th Street, New York, NY 10001, pp. 847, (2003), three pages.
Ridgway et al. "'Knobs-Into-Holes' Engineering of Antibody $C_H3$ Domains for Heavy Chain Heterodimerization," *Protein Engineering* 9(7):617-621, (1996).
Roitt et al. "Molecules which Recognize Antigen," in *Immunology*, Gower Medical Publishing, New York, pp. 5.8-5.9, (1989), four pages.
Roitt et al. "Enzymic Cleavage of Human IgG1," *Immunology, Moscow*, "*Mir*" pp. 110-111, (2000), (with English Translation).
Roselli et al. "In Vivo Comparison of CHX-DTPA Ligand Isomers in Athymic Mice Bearing Carcinoma Xenografts," *Cancer Biotherapy & Radiopharmaceuticals* 14(3):209-220, (1999).
Ruegg et al. "Improved in Vivo Stability and Tumor Targeting of Bismuth-Labeled Antibody," *Cancer Research* 50:4221-4226, (Jul. 15, 1990).
Schröder et al. "Formation of Peptide Bond," in *The Peptides: Methods of Peptide Synthesis*, Academic Press Inc., 111 Fifth Avenue, New York, New York 10003, 1:76-136, (1965).
Shen et al. "Single Variable Domain Antibody as a Versatile Building Block for the Construction of IgG-like Bispecific Antibodies," *Journal of Immunological Methods* 318:65-74, (2007).
Sidhu et al. "Phage-displayed Antibody Libraries of Synthetic Heavy Chain Complementarity Determining Regions," *J. Mol. Biol.* 338:299-310, (2004).
Singh et al. "Labeling of Antibodies by in Situ Modification of Thiol Groups Generated From Selenol-Catalyzed Reduction of Native Disulfide Bonds," *Analytical Biochemistry* 304(2):147-156, (May 15, 2002).
Stella et al. "Prodrugs: A Chemical Approach to Targeted Drug Delivery," in *Directed Drug Delivery*, Borchardt, et al., (eds.), pp. 247-267, Humana Press, (1985).
Tinianow et al. "Site-specifically $^{89}$Zr-labeled Monoclonal Antibodies for ImmunoPET," *Nuclear Medicine and Biology* 37(3):289-297, (2010).
Van Dijk. "Human Antibodies as Next Generation Therapeutics," *Curr. Opin. Pharmacol.* 5:368-374, (2001).
Verel et al. "Quantitative $^{89}$Zr Immuno-PET for in Vivo Scouting of $^{90}$Y-Labeled Monoclonal Antibodies in Xenograft-bearing Nude Mice," *The Journal of Nuclear Medicine* 44(10):1663-1670, (Oct. 2003).
Vollmers et al. "Death by Stress: Natural IgM-induced Apoptosis," *Methods and Findings in Experimental and Clinical Pharmacology* 27(3):185-191, (2005).
Vollmers et al. "The "Early Birds": Natural IgM Antibodies and Immune Surveillance," *Histology and Histopathology* 20:927-937, (2005).
Weldon et al. "A Guide to Taming a Toxin-Recombinant Immunotoxins Constructed From Pseudomonas Exotoxin a for the Treatment of Cancer," *FEBS Journal* 278(23):4683-4700, (Dec. 2011; e-published on Jun. 2, 2011).

(56) References Cited

OTHER PUBLICATIONS

Wiedemann et al. "Molecular and Structural Analysis of a Continuous Birch Profilin Epitope Defined by a Monoclonal Antibody," *The Journal of Biological Chemistry* 271(47):29915-29921, (Nov. 22, 1996).

Wilman. "Prodrugs in Cancer Chemotherapy" *Biochemical Society Transactions*, 615th Meeting Belfast, 14:375-382, (1986).

Winter et al. "Making Antibodies by Phage Display Technology," *Ann. Rev. Immunol.* 12:433-455, (1994).

Wu et al. "Arming Antibodies: Prospects and Challenges for Immunoconjugates," *Nature Biotechnology* 23(9):1137-1146, (Sep. 2005).

Wu et al. "Simultaneous Targeting of Multiple Disease Mediators by a Dual-Variable-Domain Immunoglobulin," *Nature Biotechnology* 25(11):1290-1297, (Nov. 2007; e-published on Oct. 14, 2007).

Yu et al. "Interaction Between Bevacizumab and Murine VEGF-A: A Reassessment," *Investigative Opthalmology & Visual Science* 49(2):522-527, (Feb. 2008).

Zahnd et al. "Directed in Vitro Evolution and Crystallographic Analysis of a Peptide-Binding Single Chain Antibody Fragment (Scfv) with Low Picomolar Affinity," *Journal of Biological Chemistry* 279(18):18870-18877, (Apr. 30, 2004; e-published on Jan. 30, 2004).

Zola. "Using Monoclonal Antibodies: Soluble Antigens," Chapter 6 in *Monoclonal Antibodies: A Manual of Techniques*, CRC Press, Inc., pp. 147-158, (1987).

International Search Report mailed on Apr. 22, 2015 for International Application No. PCT/EP2014/079354, filed on Dec. 29, 2014, five pages.

International Search Report mailed on Mar. 11, 2015 for International Application No. PCT/EP2014/079352 filed on Dec. 29, 2014, five pages.

International Search Report mailed on Nov. 19, 2013, for International Application No. PCT/EP2013/064100, filed on Jul. 4, 2013, four pages.

Written Opinion of the International Searching Authority mailed on Apr. 22, 2015 for International Application No. PCT/EP2014/079354, filed on Dec. 29, 2014, four pages.

Written Opinion of the International Searching Authority mailed on Mar. 11, 2015 for International Application No. PCT/EP2014/079352 filed on Dec. 29, 2014, six pages.

Written Opinion of the International Searching Authority mailed on Nov. 19, 2013, for International Application No. PCT/EP2013/064100, filed on Jul. 4, 2013, four pages.

\* cited by examiner

SEQUENCE LISTING

```
<160> NUMBER OF SEQ ID NOS: 33

<210> SEQ ID NO 1
<211> LENGTH: 5
<212> TYPE: PRT
<213> ORGANISM: Mus musculus

<400> SEQUENCE: 1

Asp Thr Phe Phe Gln
1               5

<210> SEQ ID NO 2
<211> LENGTH: 17
<212> TYPE: PRT
<213> ORGANISM: Mus musculus

<400> SEQUENCE: 2

Arg Ile Asp Pro Ala Asn Gly Phe Thr Lys Tyr Asp Pro Lys Phe Gln
1               5                   10                  15

Gly

<210> SEQ ID NO 3
<211> LENGTH: 11
<212> TYPE: PRT
<213> ORGANISM: Mus musculus
```

```
<400> SEQUENCE: 3

Trp Asp Thr Tyr Gly Ala Ala Trp Phe Ala Tyr
1               5                   10

<210> SEQ ID NO 4
<211> LENGTH: 120
<212> TYPE: PRT
<213> ORGANISM: Mus musculus

<400> SEQUENCE: 4

Glu Val Gln Leu Gln Gln Ser Gly Ala Glu Leu Val Lys Pro Gly Ala
1               5                   10                  15

Ser Val Lys Leu Ser Cys Thr Ser Gly Phe Asn Asn Lys Asp Thr
            20                  25                  30

Phe Phe Gln Trp Val Lys Gln Arg Pro Glu Glu Cys Leu Glu Trp Ile
            35                  40                  45

Gly Arg Ile Asp Pro Ala Asn Gly Phe Thr Lys Tyr Asp Pro Lys Phe
        50                  55                  60

Gln Gly Lys Ala Thr Ile Thr Val Asp Thr Ser Asn Thr Ala Tyr
65                  70                  75                  80

Leu Gln Leu Asn Ser Leu Thr Ser Glu Asp Thr Ala Leu Tyr Tyr Cys
                85                  90                  95

Thr Arg Trp Asp Thr Tyr Gly Ala Ala Trp Phe Ala Tyr Trp Gly Gln
            100                 105                 110

Gly Thr Leu Val Thr Val Ser Ala
        115                 120

<210> SEQ ID NO 5
<211> LENGTH: 11
<212> TYPE: PRT
<213> ORGANISM: Mus musculus

<400> SEQUENCE: 5

Arg Ala Ser Gly Asn Ile His Asn Tyr Leu Ser
1               5                   10

<210> SEQ ID NO 6
<211> LENGTH: 7
<212> TYPE: PRT
<213> ORGANISM: Mus musculus

<400> SEQUENCE: 6

Ser Ala Lys Thr Leu Ala Asp
1               5

<210> SEQ ID NO 7
<211> LENGTH: 9
<212> TYPE: PRT
<213> ORGANISM: Mus musculus

<400> SEQUENCE: 7

Gln His Phe Trp Ser Ser Ile Tyr Thr
1               5

<210> SEQ ID NO 8
<211> LENGTH: 107
<212> TYPE: PRT
<213> ORGANISM: Mus musculus

<400> SEQUENCE: 8

Asp Ile Gln Met Thr Gln Ser Pro Ala Ser Leu Ser Ala Ser Val Gly
```

```
                1               5                   10                  15
            Glu Thr Val Thr Ile Thr Cys Arg Ala Ser Gly Asn Ile His Asn Tyr
                            20                  25                  30

Leu Ser Trp Phe Gln Gln Lys Gln Gly Lys Ser Pro Gln Leu Leu Val
                        35                  40                  45

Tyr Ser Ala Lys Thr Leu Ala Asp Gly Val Pro Ser Arg Phe Ser Gly
                    50                  55                  60

Ser Gly Ser Gly Thr Gln Tyr Ser Leu Lys Ile Asn Ser Leu Gln Pro
            65                  70                  75                  80

Glu Asp Phe Gly Thr Tyr Tyr Cys Gln His Phe Trp Ser Ser Ile Tyr
                            85                  90                  95

Thr Phe Gly Cys Gly Thr Lys Leu Glu Ile Lys
                        100                 105

<210> SEQ ID NO 9
<211> LENGTH: 5
<212> TYPE: PRT
<213> ORGANISM: Artificial Sequence
<220> FEATURE:
<223> OTHER INFORMATION: humanized HVR-H1

<400> SEQUENCE: 9

Asp Thr Phe Phe Gln
1               5

<210> SEQ ID NO 10
<211> LENGTH: 17
<212> TYPE: PRT
<213> ORGANISM: Artificial Sequence
<220> FEATURE:
<223> OTHER INFORMATION: humanized HVR-H2

<400> SEQUENCE: 10

Arg Ile Asp Pro Ala Asn Gly Phe Thr Lys Tyr Ala Gln Lys Phe Gln
1               5                   10                  15

Gly

<210> SEQ ID NO 11
<211> LENGTH: 11
<212> TYPE: PRT
<213> ORGANISM: Artificial Sequence
<220> FEATURE:
<223> OTHER INFORMATION: humanized HVR-H3

<400> SEQUENCE: 11

Trp Asp Thr Tyr Gly Ala Ala Trp Phe Ala Tyr
1               5                   10

<210> SEQ ID NO 12
<211> LENGTH: 120
<212> TYPE: PRT
<213> ORGANISM: Artificial Sequence
<220> FEATURE:
<223> OTHER INFORMATION: humanized VH

<400> SEQUENCE: 12

Gln Val Gln Leu Val Gln Ser Gly Ala Glu Val Lys Lys Pro Gly Ser
1               5                   10                  15

Ser Val Lys Val Ser Cys Lys Ser Ser Gly Phe Asn Asn Lys Asp Thr
            20                  25                  30

Phe Phe Gln Trp Val Arg Gln Ala Pro Gly Gln Gly Leu Glu Trp Met
        35                  40                  45
```

```
Gly Arg Ile Asp Pro Ala Asn Gly Phe Thr Lys Tyr Ala Gln Lys Phe
         50                  55                  60

Gln Gly Arg Val Thr Ile Thr Ala Asp Thr Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Trp Asp Thr Tyr Gly Ala Ala Trp Phe Ala Tyr Trp Gly Gln
            100                 105                 110

Gly Thr Leu Val Thr Val Ser Ser
        115                 120

<210> SEQ ID NO 13
<211> LENGTH: 11
<212> TYPE: PRT
<213> ORGANISM: Artificial Sequence
<220> FEATURE:
<223> OTHER INFORMATION: humanized HVR-L1

<400> SEQUENCE: 13

Arg Ala Ser Gly Asn Ile His Asn Tyr Leu Ser
 1               5                  10

<210> SEQ ID NO 14
<211> LENGTH: 7
<212> TYPE: PRT
<213> ORGANISM: Artificial Sequence
<220> FEATURE:
<223> OTHER INFORMATION: humanized HVR-L2

<400> SEQUENCE: 14

Ser Ala Lys Thr Leu Ala Asp
 1               5

<210> SEQ ID NO 15
<211> LENGTH: 9
<212> TYPE: PRT
<213> ORGANISM: Artificial Sequence
<220> FEATURE:
<223> OTHER INFORMATION: humanized HVR-L3

<400> SEQUENCE: 15

Gln His Phe Trp Ser Ser Ile Tyr Thr
 1               5

<210> SEQ ID NO 16
<211> LENGTH: 107
<212> TYPE: PRT
<213> ORGANISM: Artificial Sequence
<220> FEATURE:
<223> OTHER INFORMATION: humanized VL

<400> SEQUENCE: 16

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gly Asn Ile His Asn Tyr
             20                  25                  30

Leu Ser Trp Tyr Gln Gln Lys Pro Gly Lys Val Pro Lys Leu Leu Ile
         35                  40                  45

Tyr Ser Ala Lys Thr Leu Ala Asp Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80
```

Glu Asp Val Ala Thr Tyr Tyr Cys Gln His Phe Trp Ser Ser Ile Tyr
                85                  90                  95

Thr Phe Gly Gln Gly Thr Lys Leu Glu Ile Lys
            100                 105

<210> SEQ ID NO 17
<211> LENGTH: 5
<212> TYPE: PRT
<213> ORGANISM: Artificial Sequence
<220> FEATURE:
<223> OTHER INFORMATION: VH53C HVR-H1

<400> SEQUENCE: 17

Asp Thr Phe Phe Gln
1               5

<210> SEQ ID NO 18
<211> LENGTH: 17
<212> TYPE: PRT
<213> ORGANISM: Artificial Sequence
<220> FEATURE:
<223> OTHER INFORMATION: VH53C HVR-H2

<400> SEQUENCE: 18

Arg Ile Asp Pro Cys Asn Gly Phe Thr Lys Tyr Ala Gln Lys Phe Gln
1               5                   10                  15

Gly

<210> SEQ ID NO 19
<211> LENGTH: 11
<212> TYPE: PRT
<213> ORGANISM: Artificial Sequence
<220> FEATURE:
<223> OTHER INFORMATION: VH53C HVR-H3

<400> SEQUENCE: 19

Trp Asp Thr Tyr Gly Ala Ala Trp Phe Ala Tyr
1               5                   10

<210> SEQ ID NO 20
<211> LENGTH: 120
<212> TYPE: PRT
<213> ORGANISM: Artificial Sequence
<220> FEATURE:
<223> OTHER INFORMATION: VH53C VH

<400> SEQUENCE: 20

Gln Val Gln Leu Val Gln Ser Gly Ala Glu Val Lys Lys Pro Gly Ser
1               5                   10                  15

Ser Val Lys Val Ser Cys Lys Ser Gly Phe Asn Asn Lys Asp Thr
            20                  25                  30

Phe Phe Gln Trp Val Arg Gln Ala Pro Gly Gln Gly Leu Glu Trp Met
        35                  40                  45

Gly Arg Ile Asp Pro Cys Asn Gly Phe Thr Lys Tyr Ala Gln Lys Phe
    50                  55                  60

Gln Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Asp Thr Tyr Gly Ala Ala Trp Phe Ala Tyr Trp Gly Gln
            100                 105                 110

-continued

```
Gly Thr Leu Val Thr Val Ser Ser
        115                 120

<210> SEQ ID NO 21
<211> LENGTH: 11
<212> TYPE: PRT
<213> ORGANISM: Artificial Sequence
<220> FEATURE:
<223> OTHER INFORMATION: VH53C HVR-L1

<400> SEQUENCE: 21

Arg Ala Ser Gly Asn Ile His Asn Tyr Leu Ser
1               5                   10

<210> SEQ ID NO 22
<211> LENGTH: 7
<212> TYPE: PRT
<213> ORGANISM: Artificial Sequence
<220> FEATURE:
<223> OTHER INFORMATION: VH53C HVR-L2

<400> SEQUENCE: 22

Ser Ala Lys Thr Leu Ala Asp
1               5

<210> SEQ ID NO 23
<211> LENGTH: 9
<212> TYPE: PRT
<213> ORGANISM: Artificial Sequence
<220> FEATURE:
<223> OTHER INFORMATION: VH53C HVR-L3

<400> SEQUENCE: 23

Gln His Phe Trp Ser Ser Ile Tyr Thr
1               5

<210> SEQ ID NO 24
<211> LENGTH: 107
<212> TYPE: PRT
<213> ORGANISM: Artificial Sequence
<220> FEATURE:
<223> OTHER INFORMATION: VH53C VL

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys Arg Ala Ser Gly Asn Ile His Asn Tyr
            20                  25                  30

Leu Ser Trp Tyr Gln Gln Lys Pro Gly Lys Val Pro Lys Leu Leu Ile
        35                  40                  45

Tyr Ser Ala Lys Thr Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln His Phe Trp Ser Ser Ile Tyr
                85                  90                  95

Thr Phe Gly Gln Gly Thr Lys Leu Glu Ile Lys
            100                 105

<210> SEQ ID NO 25
<211> LENGTH: 107
<212> TYPE: PRT
<213> ORGANISM: Homo sapiens
```

```
<400> SEQUENCE: 25

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 26
<211> LENGTH: 105
<212> TYPE: PRT
<213> ORGANISM: Homo sapiens

<400> SEQUENCE: 26

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105

<210> SEQ ID NO 27
<211> LENGTH: 330
<212> TYPE: PRT
<213> ORGANISM: Homo sapiens

<400> SEQUENCE: 27

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
```

```
                    100                 105                 110
Pro Ala Pro Glu Leu Leu Gly Gly Pro Ser Val Phe Leu Phe Pro Pro
            115                 120                 125
Lys Pro Lys Asp Thr Leu Met Ile Ser Arg Thr Pro Glu Val Thr Cys
        130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 28
<211> LENGTH: 330
<212> TYPE: PRT
<213> ORGANISM: Homo sapiens

<400> SEQUENCE: 28

Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
        115                 120                 125
Lys Pro Lys Asp Thr Leu Met Ile Ser Arg Thr Pro Glu Val Thr Cys
    130                 135                 140
```

```
Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 29
<211> LENGTH: 330
<212> TYPE: PRT
<213> ORGANISM: Homo sapiens

<400> SEQUENCE: 29

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190
```

```
His Gln Asp Trp Leu Asn Gly Lys Glu Tyr Lys Cys Lys Val Ser Asn
            195                 200                 205
Lys Ala Leu Pro Ala Pro Ile Glu Lys Thr Ile Ser Lys Ala Lys Gly
        210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 30
<211> LENGTH: 330
<212> TYPE: PRT
<213> ORGANISM: Homo sapiens

<400> SEQUENCE: 30

Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
        50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val Glu Pro Lys Ser Cys Asp Lys Thr His Thr Cys Pro Pro Cys
            100                 105                 110
Pro Ala Pro Glu Ala Ala Gly Gly Pro Ser Val Phe Leu Phe Pro Pro
        115                 120                 125
Lys Pro Lys Asp Thr Leu Met Ile Ser Arg Thr Pro Glu Val Thr Cys
130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Gly Ala Pro Ile Glu Lys Thr Ile Ser Lys Ala Lys Gly
210                 215                 220
Gln Pro Arg Glu Pro Gln Val Tyr Thr Leu Pro Pro Ser Arg Asp Glu
```

-continued

```
            225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
                260                 265                 270
Asn Tyr Lys Thr Thr Pro Pro Val Leu Asp Ser Asp Gly Ser Phe Phe
                275                 280                 285
Leu Tyr Ser Lys Leu Thr Val Asp Lys Ser Arg Trp Gln Gln Gly Asn
                290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 31
<211> LENGTH: 327
<212> TYPE: PRT
<213> ORGANISM: Homo sapiens

<400> SEQUENCE: 31

Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
                35                  40                  45
Gly Val His Thr Phe Pro Ala Val Leu Gln Ser Ser Gly Leu Tyr Ser
                50                  55                  60
Leu Ser Ser Val Val Thr Val Pro Ser Ser Ser Leu Gly Thr Lys Thr
65                  70                  75                  80
Tyr Thr Cys Asn Val Asp His Lys Pro Ser Asn Thr Lys Val Asp Lys
                85                  90                  95
Arg Val Glu Ser Lys Tyr Gly Pro Pro Cys Pro Ser Cys Pro Ala Pro
                100                 105                 110
Glu Phe Leu Gly Gly Pro Ser Val Phe Leu Phe Pro Pro Lys Pro Lys
                115                 120                 125
Asp Thr Leu Met Ile Ser Arg Thr Pro Glu Val Thr Cys Val Val Val
                130                 135                 140
Asp Val Ser Gln Glu Asp Pro Glu Val Gln Phe Asn Trp Tyr Val Asp
145                 150                 155                 160
Gly Val Glu Val His Asn Ala Lys Thr Lys Pro Arg Glu Glu Gln Phe
                165                 170                 175
Asn Ser Thr Tyr Arg Val Val Ser Val Leu Thr Val Leu His Gln Asp
                180                 185                 190
Trp Leu Asn Gly Lys Glu Tyr Lys Cys Lys Val Ser Asn Lys Gly Leu
                195                 200                 205
Pro Ser Ser Ile Glu Lys Thr Ile Ser Lys Ala Lys Gly Gln Pro Arg
                210                 215                 220
Glu Pro Gln Val Tyr Thr Leu Pro Pro Ser Gln Glu Glu Met Thr Lys
225                 230                 235                 240
Asn Gln Val Ser Leu Thr Cys Leu Val Lys Gly Phe Tyr Pro Ser Asp
                245                 250                 255
Ile Ala Val Glu Trp Glu Ser Asn Gly Gln Pro Glu Asn Asn Tyr Lys
                260                 265                 270
```

```
Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 32
<211> LENGTH: 327
<212> TYPE: PRT
<213> ORGANISM: Homo sapiens

<400> SEQUENCE: 32

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Glu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320
```

-continued

Leu Ser Leu Ser Leu Gly Lys
            325

<210> SEQ ID NO 33
<211> LENGTH: 327
<212> TYPE: PRT
<213> ORGANISM: Homo sapiens

<400> SEQUENCE: 33

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Glu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Gly Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
            325

ANTI-BIOTIN ANTIBODIES AND METHODS OF USE

CROSS REFERENCE TO RELATED APPLICATIONS

This application is a continuation of International Application No. PCT/EP2013/064099 having an international filing date of Jul. 4, 2013, the entire contents of which are incorporated herein by reference, and which claims benefit under 35 U.S.C. §119 to European Patent Application No. 12174957.6, filed Jul. 4, 2012.

SEQUENCE LISTING

The instant application contains a Sequence Listing submitted via EFS-Web. Said ASCII copy, created on Dec. 16, 2014, is named P31086_US_C_SeqList.txt., and is 32,034 bytes in size.

FIELD OF THE INVENTION

The present invention relates to anti-biotin antibodies and anti-biotin derivative antibodies and methods of using the same.

BACKGROUND

Hapten-binding antibodies can be applied as capturing modules for therapeutic and diagnostic applications. For example, hapten-bound entities such as fluorophores, chelating reagents, peptides, nucleic acids, proteins, lipids, nanoparticles, and many other agents can react with hapten-binding antibodies and antibody derivatives. This enables effective detection of such 'payloads', as well as capturing, accumulation at desired locations, crosslinking and other antibody-mediated effects. Since the features and composition of haptens may influence the composition and "behavior" of hapten-bound entities (incl. size, solubility, activity, biophysical properties, PK, biological effects and more), it is highly desired to develop a variety of different hapten-binding entities. Thereby, it is possible to match a selected hapten with a given payload to generate optimized hapten conjugates. Subsequently, optimal hapten-binding entities can be combined with said conjugates to generate optimal antibody-hapten-payload complexes. It is further desired to have hapten-binding entities such as antibody derivatives which are humanized. This enables applications with significantly reduced risk of interference such as immunogenicity in therapeutic applications. The antibodies that are described here bind biotin derivatives (but not unmodified biotin). These antibodies are termed in this document 'biotin-binding' or 'anti-biotin' antibodies.

In WO 00/50088 biotinylated-chemokine antibody complexes are reported.

Kohen, F., et al., report the preparation and properties of anti-biotin antibodies (Methods Enzymol. 279 (1997) 451-463. Monoclonal anti-biotin antibodies simulate avidity in the recognition of biotin is reported by Bagci, H., et al. (FEBS Lett. 322 (1993) 47-50). Cao, Y., et al., report the development of a bispecific monoclonal antibody as a universal immunoprobe for detecting biotinylated macromolecules (J. Immunol. Meth. 220 (1998) 85-91).

In WO 01/34651 antibodies binding a non-naturally occurring enantiomer (L-Biotin) and their use as targeting agents are reported.

Dakshinamurti et al. report the production and characterization of monoclonal antibody to biotin (Biochem. J. 237 (1986) 477-482). A comparison of the binding of biotin and biotinylated macromolecular ligands to an anti-biotin monoclonal antibody and to streptavidin is reported by Vincent, P., et al. (J. Immunol. Meth. 165 (1993) 177-182). Berger, M., et al. (Biochem. 14 (1975) 2338-2342) report the production of antibodies that bind biotin and inhibit biotin containing enzymes.

SUMMARY

The invention provides anti-biotin antibodies and anti-biotin-derivative antibodies as well as methods of using the same.

One aspect as reported herein is a humanized anti-biotin antibody, wherein the antibody comprises (a) HVR-H3 comprising the amino acid sequence of SEQ ID NO: 11, (b) HVR-L3 comprising the amino acid sequence of SEQ ID NO: 15, and (c) HVR-H2 comprising the amino acid sequence of SEQ ID NO: 10. This antibody specifically binds to biotin.

In one embodiment the antibody further comprises (a) HVR-H1 comprising the amino acid sequence of SEQ ID NO: 09, (b) HVR-H2 comprising the amino acid sequence of SEQ ID NO: 10, and (c) HVR-H3 comprising the amino acid sequence of SEQ ID NO: 11.

In one embodiment the antibody further comprises (a) HVR-L1 comprising the amino acid sequence of SEQ ID NO: 13; (b) HVR-L2 comprising the amino acid sequence of SEQ ID NO: 14; and (c) HVR-L3 comprising the amino acid sequence of SEQ ID NO: 15.

In one embodiment the antibody comprises at position 24 of the heavy chain variable domain numbered according to Kabat the amino acid residue serine or/and comprises at position 73 of the heavy chain variable domain numbered according to Kabat the amino acid residue threonine.

In one embodiment the antibody comprises at position 60 of the heavy chain variable domain numbered according to Kabat the amino acid residue alanine and at position 61 of the heavy chain variable domain numbered according to Kabat the amino acid residue glutamine.

In one embodiment the antibody (1) comprises at position 24 of the heavy chain variable domain numbered according to Kabat the amino acid residue serine or/and comprises at position 73 of the heavy chain variable domain numbered according to Kabat the amino acid residue threonine, (2) comprises at position 60 of the heavy chain variable domain numbered according to Kabat the amino acid residue alanine, and (3) comprises at position 61 of the heavy chain variable domain numbered according to Kabat the amino acid residue glutamine.

In one embodiment the antibody comprises (a) a VH sequence having at least 95% sequence identity to the amino acid sequence of SEQ ID NO: 12; (b) a VL sequence having at least 95% sequence identity to the amino acid sequence of SEQ ID NO: 16; or (c) a VH sequence as in (a) and a VL sequence as in (b), wherein the amino acid residue at position 24 of the heavy chain variable domain numbered according to Kabat is serine or/and the amino acid residue at position 73 of the heavy chain variable domain numbered according to Kabat is threonine and the amino acid residue at position 60 of the heavy chain variable domain numbered according to Kabat is alanine, and the amino acid residue at position 61 of the heavy chain variable domain numbered according to Kabat is glutamine.

In one embodiment the antibody comprises a VH sequence of SEQ ID NO: 12.

In one embodiment the antibody comprises a VL sequence of SEQ ID NO: 16.

One aspect as reported herein is an antibody comprising a VH sequence of SEQ ID NO: 12 and a VL sequence of SEQ ID NO: 16.

In one embodiment the antibody is a full length IgG1 antibody or a full length IgG4 antibody.

In one embodiment the antibody is a monoclonal antibody.

In one embodiment the antibody is an antibody fragment that binds biotin.

One aspect as reported herein is a pharmaceutical formulation comprising the antibody as reported herein and a pharmaceutically acceptable carrier.

One aspect as reported herein is the antibody as reported herein for use as a medicament.

One aspect as reported herein is the use of the antibody as reported herein in the manufacture of a medicament.

DETAILED DESCRIPTION OF EMBODIMENTS OF THE INVENTION

I. DEFINITIONS

Figure 1:
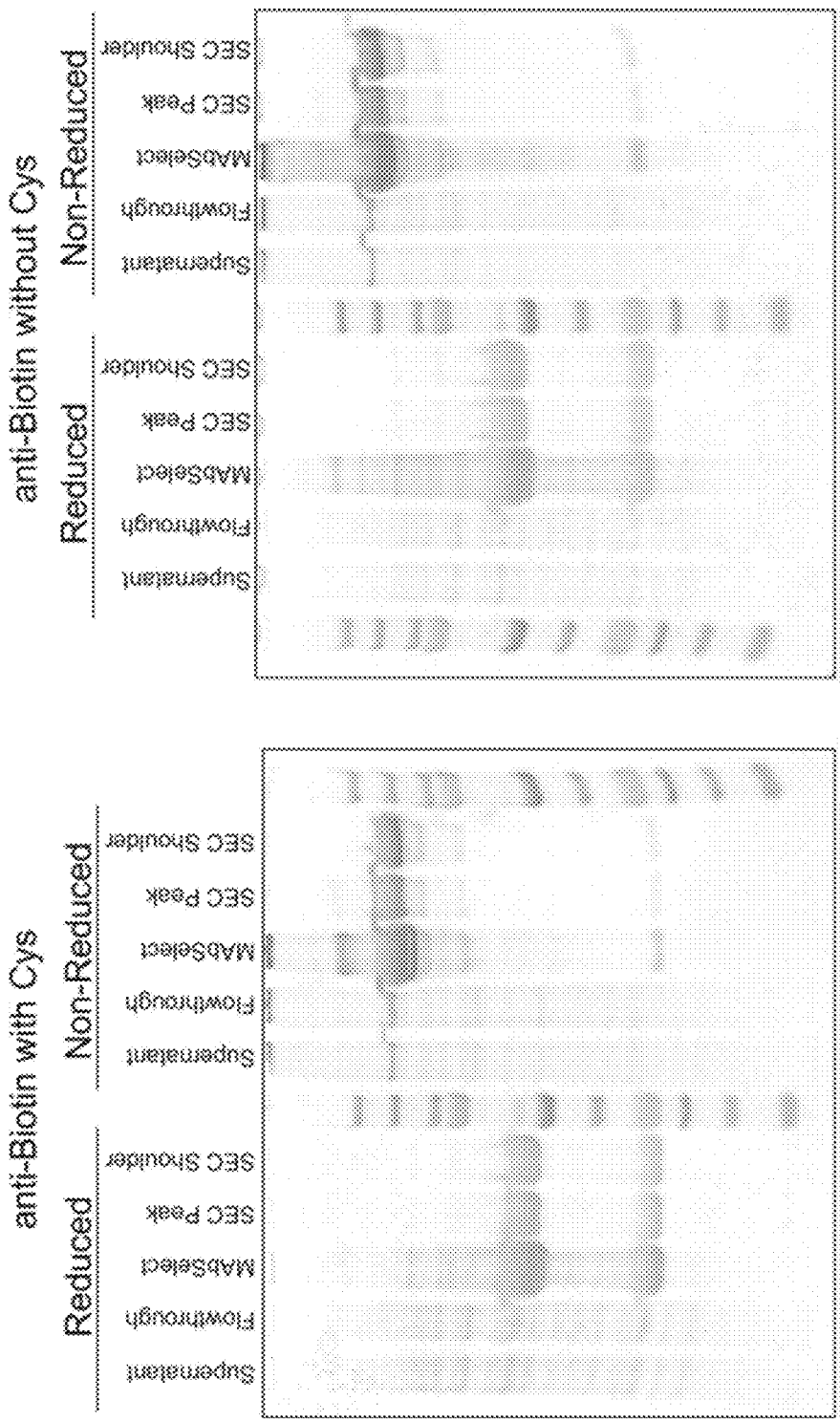
FIG. 1 Expression of the humanized antibody that binds biotin and biotin derivatives with and without cys mutation for covalent payload coupling: Reducing and non-reducing SDS PAGE shows composition and homogeneity of and humanized antibodies after purification with protein A and SEC. Antibody H-chains (upper band at 50 k) and L-chains (lower band at 25 k) are detectable as unique bands in the SEC purified fractions of both antibody derivatives without presence of visible amounts of additional protein contaminations.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The terms "anti-biotin antibody" and "an antibody that binds to biotin" refer to an antibody that is capable of binding biotin with sufficient affinity such that the antibody is useful as a diagnostic and/or therapeutic agent in targeting biotin. In one embodiment, the extent of binding of an anti-biotin antibody to an unrelated, non-biotin protein is less than about 10% of the binding of the antibody to biotin as measured, e.g., by a radioimmunoassay (RIA). In certain embodiments, an antibody that binds to biotin has a dissociation constant (Kd) of ≤1 µM, ≤100 nM, ≤10 nM, ≤1 nM, ≤0.1 nM, ≤0.01 nM, or ≤0.001 nM (e.g. $10^{-8}$M or less, e.g. from $10^{-8}$M to $10^{-13}$M, e.g., from $10^{-9}$M to $10^{-13}$ M).

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called α, δ, ε, γ, and µ, respectively.

The term "cytotoxic agent" as used herein refers to a substance that inhibits or prevents a cellular function and/or causes cell death or destruction. Cytotoxic agents include, but are not limited to, radioactive isotopes (e.g., At$^{211}$, I$^{131}$, I$^{125}$, Y$^{90}$, Re$^{186}$, Re$^{188}$, Sm$^{153}$, Bi$^{212}$, P$^{32}$, Pb$^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

"Effector functions" refer to those biological activities attributable to the Fc-region of an antibody, which vary with the antibody class. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "effective amount" of an agent, e.g., a pharmaceutical formulation, refers to an amount effective, at dosages and for periods of time necessary, to achieve the desired therapeutic or prophylactic result.

The term "Fc-region" herein is used to define a C-terminal region of an immunoglobulin heavy chain that contains at least a portion of the constant region. The term includes native sequence Fc-regions and variant Fc-regions. In one embodiment, a human IgG heavy chain Fc-region extends from Cys226, or from Pro230, to the carboxyl-terminus of the heavy chain. However, the C-terminal lysine (Lys447) of the Fc-region may or may not be present. Unless otherwise specified herein, numbering of amino acid residues in the Fc-region or constant region is according to the EU numbering system, also called the EU index, as described in Kabat, E. A., et al., Sequences of Proteins of Immunological Interest, 5th ed., Public Health Service, National Institutes of Health, Bethesda, Md. (1991), NIH Publication 91-3242.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody", "intact antibody", and "whole antibody" are used herein interchangeably to refer to an antibody having a structure substantially similar to a native antibody structure or having heavy chains that contain an Fc-region as defined herein.

The terms "host cell", "host cell line", and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat, E. A., et al., Sequences of Proteins of Immunological Interest, 5th ed., Public Health Service, National Institutes of Health, Bethesda Md. (1991), NIH Publication 91-3242, Vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR", as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3). (Chothia, C. and Lesk, A. M., J. Mol. Biol. 196 (1987) 901-917) Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat, E. A., et al., Sequences of Proteins of Immunological Interest, 5th ed. Public Health Service, National Institutes of Health, Bethesda, Md. (1991), NIH Publication 91-3242.) With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro, J. C. and Fransson, J., Front. Biosci. 13 (2008) 1619-1633). Unless otherwise indicated, HVR residues and other residues in the variable domain (e.g., FR residues) are numbered herein according to Kabat et al., supra.

An "immunoconjugate" is an antibody conjugated to one or more heterologous molecule(s), including but not limited to a cytotoxic agent.

An "individual" or "subject" is a mammal. Mammals include, but are not limited to, domesticated animals (e.g. cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman, S., et al., J. Chrom. B 848 (2007) 79-87.

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-biotin antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "biotin", as used herein, denotes 5-[(3aS,4S,6aR)-2-oxohexahydro-1H-thieno[3,4-d]imidazol-4-yl]pentanoic acid. Biotin is also known as vitamin H or coenzyme R.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt, T. J., et al., Kuby Immunology, 6th ed., W.H. Freeman and Co., N.Y. (2007), page 91) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano, S., et al., J. Immunol. 150 (1993) 880-887; Clackson, T., et al., Nature 352 (1991) 624-628).

The term "vector", as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors".

The term "hapten" denotes a small molecule that can elicit an immune response only when attached to a large carrier such as a protein. Exemplary haptens are aniline, o-, m-, and p-aminobenzoic acid, quinone, hydralazine, halothane, fluorescein, biotin, digoxigenin, theophylline and dinitrophenol. In one embodiment the hapten is biotin or digoxigenin or theophylline or carborane.

The term "a hapten that is conjugated to" or "haptenylated compound" denotes to a hapten which is covalently linked to a further moiety such as a polypeptide or a label. Activated hapten derivatives are often used as starting materials for the formation of such conjugates. In one embodiment the hapten is digoxigenin and it is conjugated (in one embodiment via its 3-hydroxy group) to the moiety via a linker. In one embodiment the linker comprises a) one or more (in one embodiment three to six) methylene-carboxy-methyl groups ($—CH_2—C(O)—$), and/or b) from 1 to 10 (in one embodiment from 1 to 5) amino acid residues (in one embodiment selected from glycine, serine, glutamate, β-alanine, γ-aminobutyric acid, ε-aminocaproic acid or lysine), and/or c) one or more (in one embodiment one or two) compounds having the structural formula $NH_2—[(CH_2)_nO]_xCH_2—CH_2—COOH$ in which n is 2 or 3 and x is 1 to 10, in one embodiment 1 to 7. The last element results (at least partly) in a linker (part) of the formula $—NH—[(CH_2)_nO]—CH_2—CH_2—C(O)—$. One example of such a compound is e.g. 12-amino-4,7,10-trioxadodecanoic acid (results in a TEG (triethylenglycol) linker). In one embodiment the linker further comprises a maleimido group. The linker has a stabilizing and solubilizing effect since it contains charges or/and can form hydrogen bridges. In addition it can sterically facilitate the binding of the anti-hapten antibody to the hapten-conjugated polypeptide. In one embodiment the linker is located at a side chain of an amino acid of the polypeptide (e.g. conjugated to a lysine or cysteine side chain via an amino or thiol group). In one embodiment the linker is located at the amino terminus or at the carboxy terminus of the polypeptide. The position of the linker on the polypeptide is typically chosen at a region where the biological activity of the polypeptide is not affected. Therefore the attachment position of the linker depends on the nature of the polypeptide and the relevant structure elements which are responsible for the biological activity. The biological activity of the polypeptide to which the hapten attached can be tested in an in vitro assay.

The term "covalent complex formation" denotes that after the formation of a non-covalent complex, e.g. between an anti-theophylline antibody and theophylline, a covalent bond is formed between the two partners in the complex. The formation of the covalent bond takes place without the need to add further reactants.

II. COMPOSITIONS AND METHODS

In one aspect, the invention is based on antibodies that bind to biotin. These antibodies are provided herein. Antibodies of the invention are useful, e.g., as monospecific antibodies for the binding of biotinylated compounds and as multispecific antibodies for the diagnosis or treatment of all kinds of diseases by using the binding specificity to the biotinylated compound as universal payloading characteristic of the antibody.

A. Exemplary Anti-Biotin Antibodies

In one aspect, the invention provides isolated antibodies that bind to biotin. In certain embodiments the anti-biotin antibodies are humanized anti-biotin antibodies. In certain embodiments, the anti-biotin antibodies as reported herein bind to biotinylated compounds without interfering with the biological activity of the compound that is conjugated to biotin and specifically bound by the antibody via the biotin residue. Therefore these antibodies can be used to improve the pharmacokinetic properties of compounds conjugated to biotin (biotinylated compound) if the antibody is a monospecific antibody. Also these antibodies can be used for the targeted delivery of a biotinylated compound if the antibody is a bi- or multispecific antibody as one binding specificity is directed against biotin and can be used as universal payloading specificity whereas a second binding specificity specifically binds e.g. to a cell surface molecule and provides for the targeting characteristic/component of the bi- or multispecific antibody.

In one aspect, the invention provides an anti-biotin antibody comprising at least one, two, three, four, five, or six HVRs selected from (a) HVR-H1 comprising the amino acid sequence of SEQ ID NO: 01; (b) HVR-H2 comprising the amino acid sequence of SEQ ID NO: 02; (c) HVR-H3 comprising the amino acid sequence of SEQ ID NO:03; (d) HVR-L1 comprising the amino acid sequence of SEQ ID NO: 05; (e) HVR-L2 comprising the amino acid sequence of SEQ ID NO: 06; and (f) HVR-L3 comprising the amino acid sequence of SEQ ID NO: 07.

In one aspect, the invention provides an anti-biotin antibody comprising at least one, at least two, or all three VH HVR sequences selected from (a) HVR-H1 comprising the amino acid sequence of SEQ ID NO: 01; (b) HVR-H2 comprising the amino acid sequence of SEQ ID NO: 02; and (c) HVR-H3 comprising the amino acid sequence of SEQ ID NO: 03. In one embodiment, the antibody comprises HVR-H3 comprising the amino acid sequence of SEQ ID NO: 03. In another embodiment, the antibody comprises HVR-H3 comprising the amino acid sequence of SEQ ID NO: 03 and HVR-L3 comprising the amino acid sequence of SEQ ID NO: 07. In a further embodiment, the antibody comprises HVR-H3 comprising the amino acid sequence of SEQ ID NO: 03, HVR-L3 comprising the amino acid sequence of SEQ ID NO: 07, and HVR-H2 comprising the amino acid sequence of SEQ ID NO: 02. In a further embodiment, the antibody comprises (a) HVR-H1 comprising the amino acid sequence of SEQ ID NO: 01; (b) HVR-H2 comprising the amino acid sequence of SEQ ID NO: 02; and (c) HVR-H3 comprising the amino acid sequence of SEQ ID NO: 03.

In another aspect, the invention provides an anti-biotin antibody comprising at least one, at least two, or all three VL HVR sequences selected from (a) HVR-L1 comprising the amino acid sequence of SEQ ID NO: 05; (b) HVR-L2 comprising the amino acid sequence of SEQ ID NO: 06; and (c) HVR-L3 comprising the amino acid sequence of SEQ ID NO: 07. In one embodiment, the antibody comprises (a) HVR-L1 comprising the amino acid sequence of SEQ ID NO: 05; (b) HVR-L2 comprising the amino acid sequence of SEQ ID NO: 06; and (c) HVR-L3 comprising the amino acid sequence of SEQ ID NO: 07.

In another aspect, an anti-biotin antibody of the invention comprises (a) a VH domain comprising at least one, at least two, or all three VH HVR sequences selected from (i) HVR-H1 comprising the amino acid sequence of SEQ ID NO: 01, (ii) HVR-H2 comprising the amino acid sequence of SEQ ID NO: 02, and (iii) HVR-H3 comprising an amino acid sequence of SEQ ID NO: 03; and (b) a VL domain comprising at least one, at least two, or all three VL HVR sequences selected from (i) HVR-L1 comprising the amino acid sequence of SEQ ID NO: 05, (ii) HVR-L2 comprising the amino acid sequence of SEQ ID NO: 06, and (c) HVR-L3 comprising the amino acid sequence of SEQ ID NO: 07.

In another aspect, the invention provides an anti-biotin antibody comprising (a) HVR-H1 comprising the amino acid sequence of SEQ ID NO: 01; (b) HVR-H2 comprising the amino acid sequence of SEQ ID NO: 02; (c) HVR-H3 comprising the amino acid sequence of SEQ ID NO: 03; (d) HVR-L1 comprising the amino acid sequence of SEQ ID NO: 05; (e) HVR-L2 comprising the amino acid sequence of SEQ ID NO: 06; and (f) HVR-L3 comprising an amino acid sequence selected from SEQ ID NO: 07.

In one embodiment, the anti-biotin antibody is humanized.

In one aspect, the invention provides a humanized anti-biotin antibody comprising at least one, two, three, four, five, or six HVRs selected from (a) HVR-H1 comprising the amino acid sequence of SEQ ID NO: 09; (b) HVR-H2 comprising the amino acid sequence of SEQ ID NO: 10; (c) HVR-H3 comprising the amino acid sequence of SEQ ID NO:11; (d) HVR-L1 comprising the amino acid sequence of SEQ ID NO: 13; (e) HVR-L2 comprising the amino acid sequence of SEQ ID NO: 14; and (f) HVR-L3 comprising the amino acid sequence of SEQ ID NO: 15.

In one aspect, the invention provides a humanized anti-biotin antibody comprising at least one, at least two, or all three VH HVR sequences selected from (a) HVR-H1 comprising the amino acid sequence of SEQ ID NO: 09; (b) HVR-H2 comprising the amino acid sequence of SEQ ID NO: 10; and (c) HVR-H3 comprising the amino acid sequence of SEQ ID NO: 11. In one embodiment, the antibody comprises HVR-H3 comprising the amino acid sequence of SEQ ID NO: 11. In another embodiment, the antibody comprises HVR-H3 comprising the amino acid sequence of SEQ ID NO: 11 and HVR-L3 comprising the amino acid sequence of SEQ ID NO: 15. In a further embodiment, the antibody comprises HVR-H3 comprising the amino acid sequence of SEQ ID NO: 11, HVR-L3 comprising the amino acid sequence of SEQ ID NO: 15, and HVR-H2 comprising the amino acid sequence of SEQ ID NO: 10. In a further embodiment, the antibody comprises (a) HVR-H1 comprising the amino acid sequence of SEQ ID NO: 09; (b) HVR-H2 comprising the amino acid sequence of SEQ ID NO: 10; and (c) HVR-H3 comprising the amino acid sequence of SEQ ID NO: 11.

In another aspect, the invention provides a humanized anti-biotin antibody comprising at least one, at least two, or all three VL HVR sequences selected from (a) HVR-L1 comprising the amino acid sequence of SEQ ID NO: 13; (b) HVR-L2 comprising the amino acid sequence of SEQ ID NO: 14; and (c) HVR-L3 comprising the amino acid sequence of SEQ ID NO: 15. In one embodiment, the antibody comprises (a) HVR-L1 comprising the amino acid sequence of SEQ ID NO: 13; (b) HVR-L2 comprising the amino acid sequence of SEQ ID NO: 14; and (c) HVR-L3 comprising the amino acid sequence of SEQ ID NO: 15.

In another aspect, an antibody of the invention comprises (a) a VH domain comprising at least one, at least two, or all three VH HVR sequences selected from (i) HVR-H1 comprising the amino acid sequence of SEQ ID NO: 09, (ii) HVR-H2 comprising the amino acid sequence of SEQ ID NO: 10, and (iii) HVR-H3 comprising an amino acid sequence of SEQ ID NO: 11; and (b) a VL domain comprising at least one, at least two, or all three VL HVR sequences selected from (i) HVR-L1 comprising the amino acid sequence of SEQ ID NO: 13, (ii) HVR-L2 comprising the amino acid sequence of SEQ ID NO: 14, and (c) HVR-L3 comprising the amino acid sequence of SEQ ID NO: 15.

In another aspect, the invention provides a humanized anti-biotin antibody comprising (a) HVR-H1 comprising the amino acid sequence of SEQ ID NO: 09; (b) HVR-H2 comprising the amino acid sequence of SEQ ID NO: 10; (c) HVR-H3 comprising the amino acid sequence of SEQ ID NO: 11; (d) HVR-L1 comprising the amino acid sequence of SEQ ID NO: 13; (e) HVR-L2 comprising the amino acid sequence of SEQ ID NO: 14; and (f) HVR-L3 comprising an amino acid sequence selected from SEQ ID NO: 15.

In another aspect, the invention provides a humanized anti-biotin antibody comprising (a) HVR-H1 comprising the amino acid sequence of SEQ ID NO: 01; (b) HVR-H2 comprising the amino acid sequence of SEQ ID NO: 02; (c) HVR-H3 comprising the amino acid sequence of SEQ ID NO: 03; (d) HVR-L1 comprising the amino acid sequence of SEQ ID NO: 05; (e) HVR-L2 comprising the amino acid sequence of SEQ ID NO: 06; and (f) HVR-L3 comprising an amino acid sequence selected from SEQ ID NO: 07, wherein the amino acid residue at position 60 in the HVR-H2 is A and the amino acid residue at position 61 in the HVR-H2 is Q.

The humanized anti-biotin antibody comprises at Kabat position 60 an A and at Kabat position 61 a Q. These changes (forward mutations) were introduced to increase the binding affinity of the humanized anti-biotin antibody.

In one embodiment, a humanized anti-biotin antibody comprises HVRs as in any of the above embodiments, and further comprises an acceptor human framework, e.g. a human immunoglobulin framework or a human consensus framework. In one embodiment, a humanized anti-biotin antibody comprises a VH comprising HVR-Hs as in any of the above embodiments, and further comprises one or more of the following S at position 24, and/or T at position 73.

Kabat position 24 corresponds to residue number 24 of SEQ ID NO: 04, 12, and 20.

Kabat position 60 corresponds to residue number 61 of SEQ ID NO: 04, 12, and 20.

Kabat position 61 corresponds to residue number 62 of SEQ ID NO: 04, 12, and 20.

Kabat position 71 corresponds to residue number 72 of SEQ ID NO: 04, 12, and 20.

These changes (forward mutations) were introduced to increase the binding affinity of the humanized anti-biotin antibody.

In another aspect, an anti-biotin antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 04. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-biotin antibody comprising that sequence retains the ability to bind to biotin. In certain embodiments, a total of 1 to 10 amino acids have been substituted, inserted and/or deleted in SEQ ID NO: 04. In certain embodiments, substitutions, insertions, or deletions occur in regions outside the HVRs (i.e., in the FRs). Optionally, the anti-biotin antibody comprises the VH sequence in SEQ ID NO: 04, including post-translational modifications of that sequence. In a particular embodiment, the VH comprises one, two or three HVRs selected from: (a) HVR-H1 comprising the amino acid sequence of SEQ ID NO: 01, (b) HVR-H2 comprising the amino acid sequence of SEQ ID NO: 02, and (c) HVR-H3 comprising the amino acid sequence of SEQ ID NO: 03.

In another aspect, an anti-biotin antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 08. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-biotin antibody comprising that sequence retains the ability to bind to biotin. In certain embodiments, a total of 1 to 10 amino acids have been substituted, inserted and/or deleted in SEQ ID NO: 08. In certain embodiments, the substitutions, insertions, or deletions occur in regions outside the HVRs (i.e., in the FRs). Optionally, the anti-biotin antibody comprises the VL sequence in SEQ ID NO: 08, including post-translational modifications of that sequence. In a particular embodiment, the VL comprises one, two or three HVRs selected from (a) HVR-L1 comprising the amino acid sequence of SEQ ID NO: 05; (b) HVR-L2 comprising the amino acid sequence of SEQ ID NO: 06; and (c) HVR-L3 comprising the amino acid sequence of SEQ ID NO:07.

In another aspect, an anti-biotin antibody is provided, wherein the antibody comprises a VH as in any of the embodiments provided above, and a VL as in any of the embodiments provided above. In one embodiment, the antibody comprises the VH and VL sequences in SEQ ID NO: 04 and SEQ ID NO: 08, respectively, including post-translational modifications of those sequences.

In another aspect, a humanized anti-biotin antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 12. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-biotin antibody comprising that sequence retains the ability to bind to biotin. In certain embodiments, a total of 1 to 10 amino acids have been substituted, inserted and/or deleted in SEQ ID NO: 12. In certain embodiments, substitutions, insertions, or deletions occur in regions outside the HVRs (i.e., in the FRs). Optionally, the anti-biotin antibody comprises the VH sequence in SEQ ID NO: 12, including post-translational modifications of that sequence. In a particular embodiment, the VH comprises one, two or three HVRs selected from: (a) HVR-H1 comprising the amino acid sequence of SEQ ID NO: 09, (b) HVR-H2 comprising the amino acid sequence of SEQ ID NO: 10, and (c) HVR-H3 comprising the amino acid sequence of SEQ ID NO: 11.

In another aspect, a humanized anti-biotin antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 16. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-biotin antibody comprising that sequence retains the ability to bind to biotin. In certain embodiments, a total of 1 to 10 amino acids have been substituted, inserted and/or deleted in SEQ ID NO: 16. In certain embodiments, the substitutions, insertions, or deletions occur in regions outside the HVRs (i.e., in the FRs). Optionally, the anti-biotin antibody comprises the VL sequence in SEQ ID NO: 16, including post-translational modifications of that sequence. In a particular embodiment, the VL comprises one, two or three HVRs selected from (a) HVR-L1 comprising the amino acid sequence of SEQ ID NO: 13; (b) HVR-L2 comprising the amino acid sequence of SEQ ID NO: 14; and (c) HVR-L3 comprising the amino acid sequence of SEQ ID NO:15.

In another aspect, a humanized anti-biotin antibody is provided, wherein the antibody comprises a VH as in any of the embodiments provided above, and a VL as in any of the embodiments provided above. In one embodiment, the antibody comprises the VH and VL sequences in SEQ ID NO: 12 and SEQ ID NO: 16, respectively, including post-translational modifications of those sequences.

In a further aspect of the invention, an anti-biotin antibody according to any of the above embodiments is a monoclonal antibody, including a chimeric, humanized or human antibody. In one embodiment, an anti-biotin antibody is an antibody fragment, e.g., an Fv, Fab, Fab', scFv, diabody, or F(ab')$_2$ fragment. In another embodiment, the antibody is a full length antibody, e.g., an intact IgG1 or IgG4 antibody or other antibody class or isotype as defined herein.

In a further aspect, an anti-biotin antibody according to any of the above embodiments may incorporate any of the features, singly or in combination, as described in Sections 1-5 below:

1. Antibody Affinity

In certain embodiments, an antibody provided herein has a dissociation constant (Kd) of ≤1 µM, ≤100 nM, ≤10 nM, ≤1 nM, ≤0.1 nM, ≤0.01 nM, or ≤0.001 nM (e.g. $10^{-8}$M or less, e.g. from $10^{-8}$M to $10^{-13}$M, e.g., from $10^{-9}$M to $10^{-13}$M).

In one embodiment, Kd is measured by a radiolabeled antigen binding assay (RIA) performed with the Fab version of an antibody of interest and its antigen as described by the following assay. Solution binding affinity of FABs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen, Y., et al., J. Mol. Biol. 293 (1999) 865-881). To establish conditions for the assay, MICROTITER® multiwell plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta, L. G., et al., Cancer Res. 57 (1997) 4593-4599). The Fab of interest is then incubated overnight; however, the incubation may continue for a longer period (e.g., about 65 hours) to ensure that equilibrium is reached.

Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, Kd is measured using surface plasmon resonance assays using a BIACORE®-2000 or a BIACORE ®-3000 (BIAcore, Inc., Piscataway, N.J.) at 25° C. with immobilized antigen CM5 chips at ~10 response units (RU). Briefly, carboxymethylated dextran biosensor chips (CM5, BIACORE, Inc.) are activated with N-ethyl-N'- (3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates ($k_{on}$) and dissociation rates ($k_{off}$) are calculated using a simple one-to-one Langmuir binding model (BIACORE ® Evaluation Software version 3.2) by simultaneously fitting the association and dissociation sensorgrams. The equilibrium dissociation constant (Kd) is calculated as the ratio $k_{off}/k_{on}$. See, e.g., Chen, Y., et al., J. Mol. Biol. 293 (1999) 865-881. If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation =295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'—SH, F(ab')$_2$, Fv, and scFv fragments, and other fragments described below. For a review of certain antibody fragments, see Hudson, P. J., et al., Nat. Med. 9 (2003) 129-134. For a review of scFv fragments, see, e.g., Plueckthun, A., In: The Pharmacology of Monoclonal Antibodies, Vol. 113, Rosenburg and Moore (eds.), Springer-Verlag, New York (1994), pp. 269-315; see also WO 93/16185; and U.S. Pat. No. 5,571,894 and U.S. Pat. No. 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 0 404 097; WO 1993/01161; Hudson, P. J., et al., Nat. Med. 9 (2003) 129-134; and Holliger, P., et al., Proc. Natl. Acad. Sci. USA 90 (1993) 6444-6448. Triabodies and tetrabodies are also described in Hudson, P. J., et al., Nat. Med. 9 (2003) 129-134).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, M A; see, e.g., U.S. Pat. No. 6,248,516 B1).

Antibody fragments can be made by various techniques, including but not limited to proteolytic digestion of an intact antibody as well as production by recombinant host cells (e.g. E. coli or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison, S. L., et al., Proc. Natl. Acad. Sci. USA 81 (1984) 6851-6855). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro, J. C. and Fransson, J., Front. Biosci. 13 (2008) 1619-1633, and are further described, e.g., in Riechmann, I., et al., Nature 332 (1988) 323-329; Queen, C., et al., Proc. Natl. Acad. Sci. USA 86 (1989) 10029-10033; U.S. Pat. No. 5,821,337; U.S. Pat. Nos. 7,527,791; 6,982,321; 7,087,409; Kashmiri, S. V., et al., Methods 36 (2005) 25-34 (describing SDR (a-CDR) grafting); Padlan, E. A., Mol. Immunol. 28 (1991) 489-498 (describing "resurfacing"); Dall'Acqua, W. F., et al., Methods 36 (2005) 43-60 (describing "FR shuffling"); and Osbourn, J., et al., Methods 36 (2005) 61-68 and Klimka, A., et al., Br. J. Cancer 83 (2000) 252-260 (describing the "guided selection" approach to FR shuffling).

Human framework regions that may be used for humanization include but are not limited to: framework regions selected using the "best-fit" method (see, e.g., Sims, M. J., et al., J. Immunol. 151 (1993) 2296-2308; framework regions derived from the consensus sequence of human antibodies of a particular subgroup of light or heavy chain variable regions (see, e.g., Carter, P., et al., Proc. Natl. Acad. Sci. USA 89 (1992) 4285-4289; and Presta, L. G., et al., J. Immunol. 151 (1993) 2623-2632); human mature (somatically mutated) framework regions or human germline framework regions (see, e.g., Almagro, J. C. and Fransson, J., Front. Biosci. 13 (2008) 1619-1633); and framework regions derived from screening FR libraries (see, e.g., Baca, M., et al., J. Biol. Chem. 272 (1997) 10678-10684 and Rosok, M. J., et al., J. Biol. Chem. 271 (19969 22611-22618).

4. Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for biotin and the other is for any other antigen. In certain embodiments, bispecific antibodies may bind to two different epitopes of biotin. Bispecific antibodies may also be used to localize cytotoxic agents to cells which express biotin. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein, C. and Cuello, A. C., Nature 305 (1983) 537-540, WO 93/08829, and Traunecker, A., et al., EMBO J. 10 (1991) 3655-3659), and "knob-in-hole" engineering (see, e.g., U.S. Pat. No. 5,731,168). Multispecific antibodies may also be made by engineering electrostatic steering effects for making antibody Fc-heterodimeric molecules (WO 2009/089004); cross-linking two or more antibodies or fragments (see, e.g., U.S. Pat. No. 4,676,980, and Brennan, M., et al., Science 229 (1985) 81-83); using leucine zippers to produce bi-specific antibodies (see, e.g., Kostelny, S. A., et al., J. Immunol. 148 (1992) 1547-1553; using "diabody" technology for making bispecific antibody fragments (see, e.g., Holliger, P., et al., Proc. Natl. Acad. Sci. USA 90 (1993) 6444-6448); and using single-chain Fv (sFv) dimers (see, e.g. Gruber, M., et al., J. Immunol. 152 (1994) 5368-5374); and preparing trispecific antibodies as described, e.g., in Tutt, A., et al., J. Immunol. 147 (1991) 60-69).

Engineered antibodies with three or more functional antigen binding sites, including "Octopus antibodies," are also included herein (see, e.g. US 2006/0025576).

The antibody or fragment herein also includes a "Dual Acting Fab" or "DAF" comprising an antigen binding site that binds to biotin as well as another, different antigen (see, US 2008/0069820, for example).

The antibody or fragment herein also includes multispecific antibodies described in WO 2009/080251, WO 2009/080252, WO 2009/080253, WO 2009/080254, WO 2010/112193, WO 2010/115589, WO 2010/136172, WO 2010/145792, and WO 2010/145793.

5. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "preferred substitutions". More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, Ile;
(2) neutral hydrophilic: Cys, Ser, Thr, Asn, Gln;

(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, P. S., Methods Mol. Biol. 207 (2008) 179-196), and/or SDRs (a-CDRs), with the resulting variant VH or VL being tested for binding affinity. Affinity maturation by constructing and reselecting from secondary libraries has been described, e.g., in Hoogenboom, H. R., et al. in Methods in Molecular Biology 178 (2002) 1-37. In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham, B. C. and Wells, J. A., Science 244 (1989) 1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

One preferred variant is a single cysteine variant wherein the amino acid residue at position 53 according to Kabat in the heavy chain variable domain is cysteine.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc-region, the carbohydrate attached thereto may be altered. Native antibodies produced by mammalian cells typically comprise a branched, biantennary oligosaccharide that is generally attached by an N-linkage to Asn297 of the CH2 domain of the Fc-region. See, e.g., Wright, A. and Morrison, S. L., TIBTECH 15 (1997) 26-32. The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc-region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc-region (EU numbering of Fc-region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US 2003/0157108; US 2004/0093621. Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO 2005/053742; WO 2002/031140; Okazaki, A., et al., J. Mol. Biol. 336 (2004) 1239-1249; Yamane-Ohnuki, N., et al., Biotech. Bioeng. 87 (2004) 614-622. Examples of cell lines capable of producing defucosylated antibodies include Lec13 CHO cells deficient in protein fucosylation (Ripka, J., et al., Arch. Biochem. Biophys. 249 (1986) 533-545; US 2003/0157108; and WO 2004/056312, especially at Example 11), and knockout cell lines, such as alpha-1,6-fucosyltransferase gene, FUT8, knockout CHO cells (see, e.g., Yamane-Ohnuki, N., et al., Biotech. Bioeng. 87 (2004) 614-622; Kanda, Y., et al., Biotechnol. Bioeng. 94 (2006) 680-688; and WO 2003/085107).

Antibodies variants are further provided with bisected oligosaccharides, e.g., in which a biantennary oligosaccharide attached to the Fc-region of the antibody is bisected by GlcNAc. Such antibody variants may have reduced fucosylation and/or improved ADCC function. Examples of such antibody variants are described, e.g., in WO 2003/011878; U.S. Pat. No. 6,602,684; and US 2005/0123546. Antibody variants with at least one galactose residue in the oligosaccharide attached to the Fc-region are also provided. Such antibody variants may have improved CDC function. Such antibody variants are described, e.g., in WO 1997/30087; WO 1998/58964; and WO 1999/22764.

c) Fc-Region Variants

In certain embodiments, one or more amino acid modifications may be introduced into the Fc-region of an antibody provided herein, thereby generating an Fc-region variant. The Fc-region variant may comprise a human Fc-region sequence (e.g., a human IgG1, IgG2, IgG3 or IgG4 Fc-region) comprising an amino acid modification (e.g. a substitution) at one or more amino acid positions.

In certain embodiments, the invention contemplates an antibody variant that possesses some but not all effector functions, which make it a desirable candidate for applications in which the half-life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch, J. V. and Kinet, J. P., Annu Rev. Immunol. 9 (1991) 457-492. Non-limiting examples of in vitro assays to assess ADCC activity of a molecule of interest is described in U.S. Pat. No. 5,500,362 (see, e.g. Hellstrom, I., et al., Proc. Natl. Acad. Sci. USA 83 (1986) 7059-7063; and Hellstrom, I., et al., Proc. Natl. Acad. Sci. USA 82 (1985) 1499-1502); U.S. Pat. No. 5,821,337 (see Bruggemann, M., et al., J. Exp. Med. 166 (1987) 1351-1361). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes, R., et al., Proc. Natl. Acad. Sci. USA 95 (1998) 652-656. C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro, H., et al., J. Immunol. Methods 202 (1996) 163-171; Cragg, M. S., et al., Blood 101 (2003) 1045-1052; and Cragg, M. S. and M. J. Glennie, Blood 103 (2004) 2738-2743). FcRn binding and in vivo clearance/half-life determinations can also be performed using methods known in the art (see, e.g., Petkova, S. B., et al., Int. Immunol. 18 (2006) 1759-1769).

Antibodies with reduced effector function include those with substitution of one or more of Fc-region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields, R. L., et al., J. Biol. Chem. 276 (2001) 6591-6604).

In certain embodiments, an antibody variant comprises an Fc-region with one or more amino acid substitutions which improve ADCC, e.g., substitutions at positions 298, 333, and/or 334 of the Fc-region (EU numbering of residues).

In some embodiments, alterations are made in the Fc-region that result in altered (i.e., either improved or diminished) C1q binding and/or Complement Dependent Cytotoxicity (CDC), e.g., as described in U.S. Pat. No. 6,194,551, WO 99/51642, and Idusogie, E. E., et al., J. Immunol. 164 (2000) 4178-4184.

Antibodies with increased half-lives and improved binding to the neonatal Fc receptor (FcRn), which is responsible for the transfer of maternal IgGs to the fetus (Guyer, R. L., et al., J. Immunol. 117 (1976) 587-593, and Kim, J. K., et al., J. Immunol. 24 (1994) 2429-2434), are described in US 2005/0014934. Those antibodies comprise an Fc-region with one or more substitutions therein which improve binding of the Fc-region to FcRn. Such Fc variants include those with substitutions at one or more of Fc-region residues: 238, 256, 265, 272, 286, 303, 305, 307, 311, 312, 317, 340, 356, 360, 362, 376, 378, 380, 382, 413, 424 or 434, e.g., substitution of Fc-region residue 434 (U.S. Pat. No. 7,371, 826).

See also Duncan, A. R. and Winter, G., Nature 322 (1988) 738-740; U.S. Pat. Nos. 5,648,260; 5,624,821; and WO 94/29351 concerning other examples of Fc-region variants.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc-region. Cysteine engineered antibodies may be generated as described, e.g., in U.S. Pat. No. 7,521,541.

e) Antibody Derivatives

In certain embodiments, an antibody provided herein may be further modified to contain additional non-proteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and non-proteinaceous moiety that may be selectively heated by exposure to radiation are provided. In one embodiment, the non-proteinaceous moiety is a carbon nanotube (Kam, N. W., et al., Proc. Natl. Acad. Sci. USA 102 (2005) 11600-11605). The radiation may be of any wavelength, and includes, but is not limited to, wavelengths that do not harm ordinary cells, but which heat the non-proteinaceous moiety to a temperature at which cells proximal to the antibody-non-proteinaceous moiety are killed.

B. Recombinant Methods and Compositions

Antibodies may be produced using recombinant methods and compositions, e.g., as described in U.S. Pat. No. 4,816,567. In one embodiment, isolated nucleic acid encoding an anti-biotin antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-biotin antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-biotin antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, K. A., In: Methods in Molecular Biology, Vol. 248, Lo, B. K. C. (ed.), Humana Press, Totowa, N.J. (2003), pp. 245-254, describing expression of antibody fragments in $E.\ coli$.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, T. U., Nat. Biotech. 22 (2004) 1409-1414; and Li, H., et al., Nat. Biotech. 24 (2006) 210-215.

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of $Spodoptera\ frugiperda$ cells.

Plant cell cultures can also be utilized as hosts. See, e.g., U.S. Pat. No. 5,959,177; U.S. Pat. Nos. 6,040,498; 6,420,548; 7,125,978; 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham, F. L., et al., J. Gen Virol. 36 (1977) 59-74); baby hamster kidney cells (BHK); mouse sertoli cells (TM4 cells as described, e.g., in Mather, J. P., Biol. Reprod. 23 (1980) 243-252); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather, J. P., et al., Annals N.Y. Acad. Sci. 383 (1982) 44-68; MRC 5 cells; and FS4 cells. Other useful mammalian host cell lines include Chinese hamster ovary (CHO) cells, including DHFR⁻ CHO cells (Urlaub, G., et al., Proc. Natl. Acad. Sci. USA 77 (1980) 4216-4220); and myeloma cell lines such as Y0, NS0 and Sp2/0. For a review of certain mammalian host cell lines suitable for antibody production, see, e.g., Yazaki, P. and Wu, A. M., Methods in Molecular Biology, Vol. 248, Lo, B. K. C. (ed.), Humana Press, Totowa, N.J. (2004), pp. 255-268.

C. Assays

Anti-biotin antibodies provided herein may be identified, screened for, or characterized for their physical/chemical properties and/or biological activities by various assays known in the art.

Binding Assays and Other Assays

In one aspect, an antibody of the invention is tested for its antigen binding activity, e.g., by known methods such as ELISA, Western blot, etc.

In another aspect, competition assays may be used to identify an antibody that competes with the antibodies as reported herein for binding to biotin.

In an exemplary competition assay, immobilized biotin is incubated in a solution comprising a first labeled antibody that binds to biotin and a second unlabeled antibody that is being tested for its ability to compete with the first antibody for binding to biotin. The second antibody may be present in a hybridoma supernatant. As a control, immobilized biotin is incubated in a solution comprising the first labeled antibody but not the second unlabeled antibody. After incubation under conditions permissive for binding of the first antibody to biotin, excess unbound antibody is removed, and the amount of label associated with immobilized biotin is measured. If the amount of label associated with immobilized biotin is substantially reduced in the test sample relative to the control sample, then that indicates that the second antibody is competing with the first antibody for binding to biotin. See Harlow, E. and Lane, D., Antibodies: A Laboratory Manual, Chapter 14, Cold Spring Harbor Laboratory, Cold Spring Harbor, N.Y. (1988).

D. Immunoconjugates

The invention also provides immunoconjugates comprising an anti-biotin antibody herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and EP 0 425 235 B1); an auristatin such as monomethyl auristatin drug moieties DE and DF (MMAE and MMAF) (see U.S. Pat. Nos. 5,635,483, 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman, L. M., et al., Cancer Res. 53 (1993) 3336-3342; and Lode, H. N., et al., Cancer Res. 58 (1998) 2925-2928); an anthracycline such as daunomycin or doxorubicin (see Kratz, F., et al., Curr. Med. Chem. 13 (2006) 477-523; Jeffrey, S. C., et al., Bioorg. Med. Chem. Lett. 16 (2006) 358-362; Torgov, M. Y., et al., Bioconjug. Chem. 16 (2005) 717-721; Nagy, A., et al., Proc. Natl. Acad. Sci. USA 97 (2000) 829-834; Dubowchik, G. M., et al., Bioorg. & Med. Chem. Letters 12 (2002) 1529-1532; King, H. D., et al., J. Med. Chem. 45 (20029 4336-4343; and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, *sap aonaria officinalis* inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example $TC^{99m}$ or $I^{123}$, or a spin label for nuclear magnetic resonance (NMR) imaging (also known as magnetic resonance imaging, MRI), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta, E. S., et al., Science 238 (1987) 1098-1104. Carbon-14-labeled 1-isothiocyanatobenzyl-3-methyldiethylene triamine pentaacetic acid (MX-DTPA) is an exemplary chelating agent for conjugation of radionucleotide to the antibody. See WO 94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari, R. V., et al., Cancer Res. 52 (1992) 127-131; U.S. Pat. No. 5,208,020) may be used.

The immunoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

E. Methods and Compositions for Diagnostics and Detection

The term "detecting" as used herein encompasses quantitative or qualitative detection.

In one embodiment, an anti-biotin antibody for use in a method of diagnosis or detection is provided. Such method may be an in vitro or in vivo method.

In certain embodiments, labeled anti-biotin antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

F. Pharmaceutical Formulations

Pharmaceutical formulations of an anti-biotin antibody as described herein are prepared by mixing such antibody having the desired degree of purity with one or more optional pharmaceutically acceptable carriers (Osol, A. (ed.) Remington's Pharmaceutical Sciences, 16th edition (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyl dimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as poly(vinylpyrrolidone); amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rhuPH20 (HYLENEX®, Baxter International, Inc.). Certain exemplary sHASEGPs and methods of use, including rhuPH20, are described in US 2005/0260186 and US 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO 2006/044908, the latter formulations including a histidine-acetate buffer.

The formulation herein may also contain more than one active ingredients as necessary for the particular indication being treated, preferably those with complementary activities that do not adversely affect each other. For example, it may be desirable to further provide. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methyl methacrylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences, 16th edition, Osol, A. (ed.) (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

G. Therapeutic Methods and Compositions

Any of the anti-biotin antibodies provided herein may be used in therapeutic methods.

In one aspect, an anti-biotin antibody for use as a medicament is provided. In certain embodiments, an anti-biotin antibody for use in a method of treatment is provided.

In a further aspect, the invention provides for the use of an anti-biotin antibody in the manufacture or preparation of a medicament.

In a further aspect, the invention provides pharmaceutical formulations comprising any of the anti-biotin antibodies provided herein. In one embodiment, a pharmaceutical formulation comprises any of the anti-biotin antibodies provided herein and a pharmaceutically acceptable carrier.

Antibodies of the invention can be used either alone or in combination with other agents in a therapy. For instance, an antibody of the invention may be co-administered with at least one additional therapeutic agent.

Such combination therapies noted above encompass combined administration (where two or more therapeutic agents are included in the same or separate formulations), and separate administration, in which case, administration of the antibody of the invention can occur prior to, simultaneously, and/or following, administration of the additional therapeutic agent and/or adjuvant. Antibodies of the invention can also be used in combination with radiation therapy.

An antibody of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 μg/kg to 15 mg/kg (e.g. 0.5 mg/kg-10 mg/kg) of antibody can be an initial candidate dosage for administration to the patient, whether, for example, by one or more separate administrations, or by continuous infusion. One typical daily dosage might range from about 1 μg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. The progress of this therapy is easily monitored by conventional techniques and assays.

It is understood that any of the above formulations or therapeutic methods may be carried out using an immunoconjugate of the invention in place of or in addition to an anti-biotin antibody.

III. ARTICLES OF MANUFACTURE

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate of the invention in place of or in addition to an anti-biotin antibody.

IV. EXAMPLES

The following are examples of methods and compositions of the invention. It is understood that various other embodiments may be practiced, given the general description provided above.

Example 1

Isolation and Characterization of cDNAs Encoding the VH and VL Domains of a Murine Anti-Biotin Antibody of IgG1 Class with Kappa Light Chain from Mouse Hybridoma The protein and (DNA) sequence information of the VH and VL domains of the murine hapten-biotin antibody was obtained directly from hybridoma clones. The experimental steps performed subsequently were (i) the isolation of RNA from antibody producing hybridoma cells, (ii) conversion of this RNA into cDNA, the transfer into VH and VL harboring PCR fragments, and (iii) integration of these PCR fragments into plasmids vectors for propagation in E. coli and determination of their DNA (and deduced protein) sequences.
RNA Preparation from Hybridoma Cells:

RNA was prepared from $5 \times 10^6$ antibody expressing hybridoma cells applying the RNeasy-Kit (Qiagen). Briefly, the sedimented cells were washed once in PBS and sedimented and subsequently resuspended for lysis in 500 μl RLT-Puffer (+β-ME). The cells were completely lysed by passing through a Qiashredder (Qiagen) and then subjected to the matrix-mediated purification procedure (ETOH, RNeasy columns) as described in the manufacturer's manual. After the last washing step, RNA was recovered from the columns in 50 μl RNAse-free water. The concentration of the recovered RNA was determined by quantify A260 and A280 of 1:20 diluted samples. The integrity (quality, degree of degradation) of the isolated RNA samples was analyzed by denaturing RNA gel electrophoresis on Formamide-Agarose gels (see Maniatis Manual). Discrete bands representing the intact 18s and 28 s ribosomal RNAs were obtained and intactness (and approx. 2:1 intensity ratios) of these bands indicated a good quality of the RNA preparations. The isolated RNAs from hybridoma were frozen and stored at −80 C in aliquots.
Generation of DNA Fragments Encoding VH and VH by RACE PCR, Cloning of these DNA Fragments into Plasmids and Determination of Their DNA- and Amino Acid Sequences:

The cDNA for subsequent (RACE-) PCR reactions were prepared from RNA preparations by applying the technologies as described in International patent application PCT/EP2011/074273. Subsequently, the VH and VL-encoding PCR fragments were isolated by agarose gel extraction and subsequent purification by standard molecular biology techniques. PWO-generated purified PCR fragments were inserted into the vector pCR bluntII topo by applying the pCR bluntII topo Kit (Invitrogen) exactly following the manufacturer's instructions. The Topo-ligation reactions were transformed into E. coli TopolO-one-shot competent cells. Thereafter, E. coli clones that contained vectors with either VL- or VH containing inserts were identified as colonies on LB-Kanamycin agar plates. Plasmids were prepared from these colonies and the presence of the desired insert in the vector was confirmed by restriction digestion with EcoRI. Because the vector backbone contains EcoRI restriction recognition sites flanking each side of the insert, plasmids harboring inserts were defined by having EcoRi-releasable inserts of approx. 800 bp (for VL) or 600 by (for VH). The DNA sequence and the deduced protein sequence of the VL and VH were determined by automated DNA sequencing on multiple clones for VH and VL.

The murine VL sequence of the anti-biotin antibody is depicted in SEQ ID NO: 08.

The murine VH sequence of the anti-biotin antibody is depicted in SEQ ID NO: 04.

Example 2

Humanization of the VH and VL Domains of Murine Anti-Biotin Antibody

The murine biotin-binding antibody muM33 was humanized as follows: The generation and characterization of encoding sequences and amino acid sequences that comprise the VH and VL domains of a murine anti-biotin antibody of the IgG1 class with kappa light chain from mouse hybridoma are described in WO 2011/003557 & WO 2011/003780. Based upon this information, a corresponding humanized anti-biotin antibody was generated (huM33) based on the human germline framework IGHV1-69-02 and IGKV1-27-01 combination. For VL, it was not necessary to integrate any backmutation in the framework of the human IGKV1-27-01 and the human J element of the IGKJ2-01 germline. The humanized VH is based on the human IGHV1-69-02 germline and the human J element of the IGHJ4-01-3 germline. Two backmutations in framework region 1 at position 24

(A24S) and in framework region 3 at position 73 (K73T) were introduced. The amino acid sequence of the humanized VH is depicted in SEQ ID NO: 12 and the amino acid sequence of the humanized VL is shown in SEQ ID NO: 16.

Example 3

Crystallization and X-ray Structure Determination of the Binding Region of the Murine Anti-Biotin Fv Region in the Presence of Biotin The structure of the murine anti-biotin antibody was determined. Therefore, Fab fragments were generated by protease digestion of the purified IgGs and subsequently purified, applying well known state of the art methods (papain digestion).

For crystallization of the apo Fab fragment (purified Fabs) in 20 mM His-HCl, 140 mM NaCl, pH 6.0 were concentrated to 13 mg/ml. Crystallization droplets were set up at 21° C. by mixing 0.2 µl of protein solution with 0.2 µl reservoir solution in vapor diffusion sitting drop experiments. Crystals appeared out of 0.1 M Tris pH 8.5, 0.01 M cobalt chloride, 20% polyvinylpyrrolidone K15 within 5 days and grew to a final size of 0.3 mm×0.06 mm×0.03 mm within 8 days.

Crystals were harvested with 15% Glycerol as cryoprotectant and then flash frozen in liquid N2. Diffraction images were collected with a Pilatus 6M detector at a temperature of 100K at the beam line X10SA of the Swiss Light Source and processed with the programs XDS [Kabsch, W., J. Appl. Cryst. 26 (1993) 795-800] and scaled with SCALA [obtained from BRUKER AXS], yielding data to 2.22Å resolution. This Fab fragment crystal belongs to monoclinic space group P21 with cell dimensions of a=90.23 Å b=118.45 Å c=96.79 Å and β=117.53° and contains four Fab molecules per crystallographic asymmetric unit (see Table 2).

Standard crystallographic programs from the CCP4 software suite were used to solve the structure by molecular replacement with the PDB entry 3PQP as search model, to calculate the electron density, and to refine the x-ray structure [CCP4 (Collaborative Computational Project, N. The CCP4 suite: programs for protein crystallography. Acta Crystallogr. D (1994) 760-763]. The structural models were rebuilt into the electron density using COOT (Emsley, P., et al., Acta Crystallogr. D Biol. Crystallogr. 60 (2010) 486-501). Coordinates were refined with REFMAC5 (Murshudov, G. N., et al., Acta Crystallogr. D Biol. Crystallogr. 53 (1997) 240-255) and with autoBUSTER (Global Phasing Ltd.).

TABLE 2

Data collection and structure refinement statistics for monoclinic muM33 Fab fragment apo-crystal

| Data Collection | |
|---|---|
| Wavelength (Å) | 1.0 |
| Resolution[1] (Å) | 2.22 (2.34-2.22) |
| Unique reflections[1] | 77716 (11301) |
| Completeness (%)[1] | 98.0 (100) |
| $R_{merge}$ (%)[1,2] | 6.4 (44.4) |
| $<I/\sigma>$[1] | 8.3 (1.7) |
| Unit Cell (Space group C2) | a = 90.23 Å b = 118.45 Å c = 96.73 Å and β = 117.53° |
| Refinement | |
| Resolution (Å) | 2.2 (2.28-2.22) |
| $R_{cryst}$[1,3] | 20.66 (21.84)) |
| $R_{free}$[1,4] | 25.23 (26.47) |
| Number of Atoms in refinement | 13314 |
| R.m.s. deviations from ideality Bond lengths (Å)/angles (°) | 0.01/1.21 |
| Main chain dihedral angles (%) Most favored/allowed/generous/disallowed[5] | 90.4/9.1/0.3/0.2 |

[1]Values in parentheses refer to the highest resolution bins.
[2]$R_{merge} = \Sigma|I - <I>|/\Sigma I$ where I is intensity.
[3]$R_{cryst} = \Sigma|F_o - <F_c>|/\Sigma F_o$ where $F_o$ is the observed and $F_c$ is the calculated structure factor amplitude.
[4]$R_{free}$ was calculated based on 5% of the total data omitted during refinement.
[5]Calculated with PROCHECK [Laskowski, R. A., MacArthur, M. W., Moss, D. S. & Thornton, J. M. PROCHECK: a program to check the stereochemical quality of protein structure. J. Appl. Crystallogr. 26, 283-291 (1993)].

For the crystallization of Fab-fragment in complex with a biotin-derivative apo Crystals of the Fab fragment used for soaking experiments were derived out of 0.8 M Succinic Acid within 3 days after screening and grew to a final size of 0.25 mm×0.04 mm×0.04 mm within 5 days. Biocytinamid was dissolved at 100 mM in water. Subsequently, the compound was diluted to 10 mM working concentration in crystallization solution and applied to the crystals in the crystallization droplet. Crystals were washed three times with 2 µl of 10 mM compound solution and were finally incubated for 16 h with biocytinamid at 21° C.

Crystals were harvested with 15% glycerol as cryoprotectant and then flash frozen in liquid $N_2$. Diffraction images were collected with a Pilatus 6M detector at a temperature of 100 K at the beam line X10SA of the Swiss Light Source and processed with the programs XDS [Kabsch, W., J. Appl. Cryst. 26 (1993) 795-800] and scaled with SCALA [obtained from BRUKER AXS], yielding data to 2.35 Å resolution. This Fab fragment crystal belongs to monoclinic space group P21 with cell dimensions of a=89.09 Å b=119.62 Å c=96.18 Å and β=117.15° and contains four Fab molecules per crystallographic asymmetric unit (see Table 3).

Standard crystallographic programs from the CCP4 software suite were used to solve the structure by molecular replacement with the coordinates of the apo Fab fragment as search model, to calculate the electron density, and to refine the x-ray structure to a resolution of 2.5 Å [CCP4 (Collaborative Computational Project)]. The structural models were rebuilt into the electron density using COOT (Emsley, P., et al., Acta Crystallogr. D Biol. Crystallogr. 60 (2010) 486-501). Coordinates were refined with REFMAC5 (Murshudov, G. N., et al., Acta Crystallogr. D Biol. Crystallogr. 53 (1997) 240-255) and with autoBUSTER (Global Phasing Ltd.).

TABLE 3

Data collection and structure refinement statistics for monoclinic muM33 Fab fragment biocytinamid complex crystal

| Data Collection | |
|---|---|
| Wavelength (Å) | 1.0 |
| Resolution[1] (Å) | 2.35 (2.45-2.35) |
| Unique reflections[1] | 74645 (8714) |
| Completeness (%)[1] | 99.9 (99.9) |
| $R_{merge}$ (%)[1,2] | 6.30 (65.00) |
| $<I/\sigma>$[1] | 10.29 (1.18) |
| Unit Cell (Space group C2) | a = 89.09 Å  b = 119.62 Å  c = 96.18 Å and β = 117.15° |
| Refinement | |
| Resolution (Å) | 2.5 (2.565-2.500) |
| $R_{cryst}$[1,3] | 20.92 (36.86)) |
| $R_{free}$[1,4] | 27.56 (47.5) |
| Number of Atoms in refinement | 13656 |
| R.m.s. deviations from ideality Bond lengths (Å)/angles (°) | 0.009/1.43 |
| Main chain dihedral angles (%) Most favored/allowed/generous/disallowed[5] | 87.5/12.0/0.2/0.3 |

[1]Values in parentheses refer to the highest resolution bins.
[2]$R_{merge} = \Sigma |I - <I>|/\Sigma I$ where I is intensity.
[3]$R_{cryst} = \Sigma |F_o - <F_c>|/\Sigma F_o$ where $F_o$ is the observed and $F_c$ is the calculated structure factor amplitude.
[4]$R_{free}$ was calculated based on 5% of the total data omitted during refinement.
[5]Calculated with PROCHECK [Laskowski, R. A., et al., J. Appl. Crystallogr. 26 (1993) 283-291].

The crystal form of the complex contained four independent biocytinamid: anti-biotin Fab complexes in the asymmetric unit, with biocytinamid bound similarly by all Fab molecules. Biocytidinamide is bound in a pocket formed by CDRs 1 and 3 of the heavy chain and all 3 light chain CDRs. The binding pocket of the ligand is defined by residues ASN29, ASP31, THR32, PHE33, GLN35, TRP99 and TRP106 from the heavy chain and ASN31, TYR32, LEU33, SER34, TYR49, SER50, PHE91 and TYR96 from the light chain. The biotin head group forms hydrogen bonds with residues of CDR2 and CDR1 at one end of the pocket: N3 of biocytinamid is interacting with the hydroxyl-oxygen of Ser50 whereas O22 is in contact with the backbone-amide nitrogen of the same residue. In addition, O22 of biocytinamid is also hydrogen-bonded to the hydroxyl-group oxygen of Ser34. In addition to that, hydrophobic interactions are observed between biocytinamid and the aromatic side chains lining the binding pocket. The amide bond at the end of the $(CH_2)_4$ aliphatic tail of biotin stacks onto PHE33 of heavy chain CDR1 and is stabilized by an additional hydrogen bond to the backbone amide nitrogen of PHE33 and to Asp31. This positions the amide nitrogen, which is the site of linkage to the active entity, in a way that atoms that are following the nitrogen are pointing away from the binding pocket towards the solvent.

The results of the experimental determination of the binding region at a resolution of 2.5 Å enables the characterization of the binding mode of the ligand to its antibody, which is a prerequisite for detailed modeling and further improvement via protein engineering of recombinant biotin binding modules.

Example 4

Composition, Expression and Purification of Recombinant Anti-Biotin Antibodies

Murine and humanized anti-biotin antibody variable regions were combined with constant regions of human origin to form mono- or bispecific chimeric or humanized antibodies.

The generation of monospecific humanized anti-biotin antibodies and bispecific humanized anti-biotin antibodies that specifically bind biotin as well as a different non-biotin target (e.g. receptor tyrosine kinases or IGF-1R) required (i) design and definition of amino- and nucleotide sequences for such molecules, (ii) expression of these molecules in transfected cultured mammalian cells, and (iii) purification of these molecules from the supernatants of transfected cells. These steps were performed as previously described in PCT/EP2011/074273.

In general, to generate a humanized antibody of the IgG class that has the binding specificity of the (original) murine anti-biotin antibody, the humanized VH sequence was fused in frame to the N-terminus of CH1-hinge-CH2-CH3 of a human Fc-region of the subclass IgG1. Similarly, the humanized VL sequence was fused in frame to the N-terminus of human CLkappa constant region.

To generate bispecific antibody derivatives that contain the biotin-binding specificity as well as specificities to other targets, the anti-biotin antibody, a scFv or Fab fragment was fused in frame to the C-terminus of the heavy chain of previously described antibodies. In many cases, the applied anti-hapten scFv was further stabilized by introduction of a VH44-VL100 disulfide bond which has been previously described (e.g. Reiter, Y., et al., Nature biotechnology 14 (1996) 1239-1245).

Expression Plasmids:

Expression plasmids comprise expression cassettes for the expression of the heavy and light chains were separately assembled in mammalian cell expression vectors.

Thereby the gene segments encoding the individual elements were joined as outlined above.

General information regarding the nucleotide sequences of human light and heavy chains from which the codon usage can be deduced is given in: Kabat, E. A., et al., Sequences of Proteins of Immunological Interest, 5th ed., Public Health Service, National Institutes of Health, Bethesda, Md. (1991), NIH Publication No 91-3242.

The transcription unit of the κ-light chain is composed of the following elements:
  the immediate early enhancer and promoter from the human cytomegalovirus (hCMV),
  a synthetic 5'-UT including a Kozak sequence,
  a murine immunoglobulin heavy chain signal sequence including the signal sequence intron,
  the cloned variable light chain cDNA arranged with a unique BsmI restriction site at the 5' end and a splice donor site and a unique NotI restriction site at the 3' end,
  the genomic human κ-gene constant region, including the intron 2 mouse Ig-κ enhancer (Picard, D., and Schaffner, W. Nature 307 (1984) 80-82), and
  the human immunoglobulin κ-polyadenylation ("poly A") signal sequence.

The transcription unit of the γ1-heavy chain is composed of the following elements:
  the immediate early enhancer and promoter from the human cytomegalovirus (hCMV),
  a synthetic 5'-UT including a Kozak sequence, a modified murine immunoglobulin heavy chain signal sequence including the signal sequence intron, the cloned monospecific variable heavy chain cDNA or the cloned bispecific fusion scFv-variable heavy chain cDNA arranged with a unique BsmI restriction site at the 5' and a splice donor site and a unique NotI restriction site at the 3' end, the genomic human γ1-heavy gene constant region, including the mouse Ig μ-enhancer (Neuberger, M. S., EMBO J. 2 (1983) 1373-1378), and the human γ1-immunoglobulin polyadenylation ("polyA") signal sequence.

Beside the κ-light chain or γ1-heavy chain expression cassette these plasmids contain a hygromycin resistance gene, an origin of replication, oriP, of Epstein-Barr virus (EBV), an origin of replication from the vector pUC18 which allows replication of this plasmid in E. coli, and a β-lactamase gene which confers ampicillin resistance in E. coli.

Recombinant DNA Techniques:

Cloning was performed using standard cloning techniques as described in Sambrook, J., et al., Molecular Cloning: A Laboratory Manual, second edition, Cold Spring Harbor Laboratory Press (1989). All molecular biological reagents were commercially available (if not indicated otherwise) and were used according to the manufacturer's instructions.

DNA that contains coding sequences, mutations or further genetic elements was synthesized by Geneart AG, Regensburg.

DNA sequences were determined by double strand sequencing performed at SequiServe (SequiServe GmbH, Germany).

DNA and Protein Sequence Analysis and Sequence Data Management:

The Vector NTI Advance suite version 9.0 was used for sequence creation, mapping, analysis, annotation, and illustration.

Expression of Anti-Biotin Antibodies and Derivatives:

The anti-biotin antibodies were expressed by transient transfection of human embryonic kidney 293 (HEK293) cells in suspension. For that, light and heavy chains of the corresponding mono- or bispecific antibodies were constructed in expression vectors carrying prokaryotic and eukaryotic selection markers as outlined above. These plasmids were amplified in E. coli, purified, and subsequently applied for transient transfections. Standard cell culture techniques were used for handling of the cells as described in Current Protocols in Cell Biology (2000), Bonifacino, J. S., Dasso, M., Harford, J. B., Lippincott-Schwartz, J. and Yamada, K. M. (eds.), John Wiley & Sons, Inc.

The cells were cultivated in appropriate expression medium at 37° C./8% $CO_2$. On the day of transfection the cells were seeded in fresh medium at a density of $1-2 \times 10^6$ viable cells/ml. The DNA-complexes with transfection reagents were prepared in Opti-MEM I medium (Invitrogen, USA) comprising 250 μg of heavy and light chain plasmid DNA in a 1:1 molar ratio for a 250 ml final transfection volume. The monospecific or bispecific antibody containing cell culture supernatants were clarified 7 days after transfection by centrifugation at 14,000 g for 30 minutes and filtration through a sterile filter (0.22 μm). Supernatants were stored at −20° C. until purification.

To determine the concentration of antibodies and derivatives in the cell culture supernatants, affinity HPLC chromatography was applied. For that, the cell culture supernatant containing mono- or bispecific antibody or derivatives thereof that bind to protein-A was applied to an Applied Biosystems Poros A/20 column in a solution comprising 200 mM $KH_2PO_4$, 100 mM sodium citrate, at pH 7.4. Elution from the chromatography material was performed by applying a solution comprising 200 mM NaCl, 100 mM citric acid, at pH 2.5. An UltiMate 3000 HPLC system (Dionex) was used. The eluted protein was quantified by UV absorbance and integration of peak areas. A purified IgG1 antibody served as a standard.

Purification of Anti-Biotin Antibodies:

Seven days after transfection the HEK 293 cell supernatants were harvested. The recombinant antibody contained therein were purified from the supernatant in two steps by affinity chromatography using protein A-Sepharose™ affinity chromatography (GE Healthcare, Sweden) and Superdex200 size exclusion chromatography. Briefly, the antibody containing clarified culture supernatants were applied on a MabSelectSuRe Protein A (5-50 ml) column equilibrated with PBS buffer (10 mM $Na_2HPO_4$, 1 mM $KH_2PO_4$, 137 mM NaCl and 2.7 mM KCl, pH 7.4). Unbound proteins were washed out with equilibration buffer. The antibodies (or -derivatives) were eluted with 50 mM citrate buffer, pH 3.2. The protein containing fractions were neutralized with 0.1 ml 2 M Tris buffer, pH 9.0. Then, the eluted protein fractions were pooled, concentrated with an Amicon Ultra centrifugal filter device (MWCO: 30 K, Millipore) and loaded on a Superdex200 HiLoad 26/60 gel filtration column (GE Healthcare, Sweden) equilibrated with 20 mM histidine, 140 mM NaCl, at pH 6.0. The protein concentration of purified antibodies and derivatives was determined by determining the optical density (OD) at 280 nm with the OD at 320 nm as the background correction, using the molar extinction coefficient calculated on the basis of the amino acid sequence according to Pace, et al., Protein Science 4 (1995) 2411-2423. Monomeric antibody fractions were pooled, snap-frozen and stored at −80° C. Part of the samples was provided for subsequent protein analytics and characterization.

The homogeneity of the antibodies was confirmed by SDS-PAGE in the presence and absence of a reducing agent (5 mM 1,4-dithiothreitol) and staining with Coomassie brilliant blue. The NuPAGE® Pre-Cast gel system (Invitrogen, USA) was used according to the manufacturer's instruction (4-20% Tris-Glycine gels).

Under reducing conditions, polypeptide chains related to the IgG showed upon SDS-PAGE at apparent molecular sizes analogous to the calculated molecular weights. Expression levels of all constructs were analyzed by protein-A. Average protein yields were between 6 mg and 35 mg of purified protein per liter of cell-culture supernatant in such non-optimized transient expression experiments.

FIG. 1 shows the results of expression and purification of the humanized antibody that binds biotin and biotin derivatives. Reducing and non-reducing SDS PAGE shows composition and homogeneity of humanized antibodies with and without cysteine at position 53 according to Kabat after purification with protein A (MabSelect) and SEC. The molecular weight marker is in the non-labeled lanes. Antibody H-chains (upper band at 50k) and L-chains (lower band at 25k) are detectable under reduced conditions as unique bands without presence of visible amounts of additional protein contaminants.

Example 5

Binding of Recombinant Humanized Anti-Biotin Antibody to Biotin-Labeled Compound (Biotinylated Compound)

The binding properties of the recombinant chimeric and humanized anti-biotin antibody and a variant thereof, which has a cysteine at position 53 in the HVR-H2 according to the numbering of Kabat, were analyzed by biolayer interferometry (BLI) technology using an Octet QK instrument (Fortebio Inc.). This system is well established for the study of molecule interactions. BLi-technology is based on the measurement of the interference pattern of white light reflected from the surface of a biosensor tip and an internal reference. Binding of molecules to the biosensor tip is resulting in a shift of the interference pattern which can be measured. To analyze if the humanization procedure described above diminished the ability of the anti-biotin antibody to bind to biotin, the properties of the chimeric and the humanized versions of the antibody in their ability to bind to a biotinylated protein were compared directly. Binding studies were performed by capturing anti-biotin antibody on anti-huIgG Fc antibody Capture (AHC) Biosensors (Fortebio Inc.). First, biosensors were incubated in an antibody solution with a concentration of 0.5 mg/ml in 20 mM histidine, 140 mM NaCl, pH 6.0 for 1 min. Thereafter, the biosensors were incubated for 1 min. in 1× PBS pH 7.4 to reach a stable baseline. Binding was measured by incubating the antibody-coated biosensors in a solution containing biotinylated protein with a concentration of 0.06 mg/ml in 20 mM histidine, 140 mM NaCl, pH 6.0 for 5 min. Dissociation was monitored for 5 min. in 1× PBS pH 7.4. The resulting binding curves for chimeric and humanized anti-biotin antibodies were compared directly.

The humanized version of the antibody showed equal or even better binding of the biotinylated antigen than the chimeric antibody. The same is true for the humanized antibody with the Cys mutation at Kabat position VH53. The biotinylated protein showed residual unspecific binding to the biosensors which was reduced when the biosensors were coated with Herceptin, which does not bind biotin. Thus, the functionality of the anti-biotin antibody was retained in its humanized variant (which is defined by the sequences as depicted in SEQ ID NO: 12 and 16, SEQ ID NO: 20 and 24).

Surface Plasmon Resonance:

Surface plasmon resonance measurement was performed on a BIAcore® T200 instrument (GE Healthcare Biosciences AB, Sweden) at 25° C. Around 4300 resonance units (RU) of the capturing system (10 μg/ml Anti-human Capture (IgG Fc) from Human Antibody Capture Kit, BR-1008-39, GE Healthcare Biosciences AB, Sweden) were coupled on a CM3 chip (GE Healthcare, BR-1005-36) at pH 5.0 by using the standard amine coupling kit supplied by GE Healthcare (BR-1000-50). The running buffer for amine coupling was HBS-N (10 mM HEPES, pH 7.4, 150 mM NaCl, GE Healthcare, BR-1006-70). Running and dilution buffer for the followed binding study was PBS-T (10 mM phosphate buffered saline including 0.05% Tween 20) pH 7.4. The humanized anti-biotin antibody was captured by injecting a 2 nM solution for 60 sec at a flow rate of 5 μl/min. Biotinylated siRNA was diluted with PBS-T at concentrations of 0.14-100 nM (1:3 dilution series). Binding was measured by injecting each concentration for 180 sec at a flow rate of 30 gl/min, dissociation time 600 sec. The surface was regenerated by 30 sec washing with a 3 M $MgCl_2$ solution at a flow rate of 5 μl/min. The data were evaluated using BIAevaluation software (GE Healthcare Biosciences AB, Sweden). Bulk refractive index differences were corrected by subtracting the response obtained from an anti-human IgG Fc surface. Blank injections were also subtracted (=double referencing). For calculation of KD and kinetic parameters the Langmuir 1:1 model was used.

Kinetic binding analysis by surface plasmon resonance (SPR) was carried out for humanized anti-biotin antibody SEQ ID NO: 12 and 16 and humanized anti-biotin antibody VH53C SEQ ID NO: 20 and 24. Anti-biotin antibodies at a concentration of 2 nM were captured by anti-human IgG Fc antibody which was bound to a CM3 sensor chip. Binding of biotinylated siRNA (Mw: 13868 Da) was recorded at the concentrations 0.41, 1.23, 3.7, 11.1, 33.3, 100 and 300 nM. Measurements were carried out in duplicates. The calculated $K_D$ for humanized anti-biotin antibody and humanized anti-biotin antibody VH53C were 0.633 nM and 0.654 nM, respectively.

Example 6

Generation of Non-Covalent Complexes of Biotinylated Compounds with Anti-Biotin Antibodies General Method:

The generation of complexes of anti-biotin antibodies with biotinylated compounds (=biotin conjugated to a payload) shall result in defined complexes and it shall be assure that the compound (=payload) in these complexes retains its activity. For the generation of complexes of biotinylated compounds with the anti-biotin antibody the biotinylated compound was dissolved in $H_2O$ to a final concentration of 1 mg/ml. The antibody was concentrated to a final concentration of 1 mg/ml (4.85 μM) in 20 mM histidine buffer, 140 mM NaCl, pH=6.0. Biotinylated payload and antibody were mixed to a 2:1 molar ratio (compound to antibody) by pipetting up and down and incubated for 15 minutes at RT.

Alternatively, the biotinylated compound was dissolved in 100% DMF to a final concentration of 10 mg/ml. The antibody was concentrated to a final concentration of 10 mg/ml in 50 mM Tris-HCl, 1 mM EDTA, pH=8.2. Biotinylated compound and antibody were mixed to a 2.5:1 molar ratio (compound to antibody) by pipetting up and down and incubated for 60 minutes at RT and 350 rpm.

Exemplary Method for the Formation of Complexes of Biotinylated Fluorescent Dyes and Anti-Biotin Antibodies—Biotin-Cy5/Chimeric Anti-Biotin Antibody (Human IgG Subclass) Complex:

For the generation of complexes of biotin-derivatized-Cy5 (Biotin-Cys-Cy5) containing a cysteinylated linker, 0.16 mg of Biotin-Cys-Cy5 were dissolved in 100% DMF to a concentration of 10 mg/ml. 1 mg of the antibody was used in a concentration of 10.1 mg/ml (about 69 μM) in a buffer composed of 50 mM Tris-HCl, 1 mM EDTA, pH 8.2. Biotin-Cys-Cy5 and antibody were mixed at a 2.5:1 molar ratio (Biotin-Cys-Cy5 to antibody) and incubated for 60 min at RT, shaken at 350 rpm. The resulting conjugate was analyzed by SDS-PAGE as described in Example 7. Detection of fluorescence was carried out as described in Example 7.

Exemplary Method for the Formation of Complexes of Biotinylated Fluorescent Dyes and Anti-Biotin Antibodies—Biotin-Cys-Cy5/Humanized Anti-Biotin Antibody:

For the generation of complexes of biotin-derivatized-Cy5 (Biotin-Cys-Cy5) containing a cysteinylated linker, 0.16 mg of Biotin-Cys-Cy5 were dissolved in 100% DMF to a concentration of 10 mg/ml. 1 mg of the antibody was used in a concentration of 5.5 mg/ml (about 38 μM) in a buffer composed of 50 mM Tris-HCl, 1 mM EDTA, pH 8.2. Biotin-Cys-Cy5 and antibody were mixed at a 2.5:1 molar ratio (Biotin-Cys-Cy5 to antibody) and incubated for 60 min at RT, shaken at 350 rpm. The resulting conjugate was analyzed by SDS-PAGE as described in Example 7. Detection of fluorescence was carried out as described in Example 7.

Exemplary Method for the Formation of Complexes of Biotinylated Polypeptides and Anti-Biotin Antibodies—Ac-PYY-PEG3-Cys-β-Ala-Biotin/Chimeric Anti-Biotin Antibody Complex:

For the generation of non-covalent complexes of biotinylated-PYY-polypeptide containing a cysteinylated linker, 0.19 mg of Ac-PYY-PEG3-Cys-β-Ala-Biotin were dissolved in 100% DMF to a concentration of 10 mg/ml. The antibody was used in a concentration of 10.7 mg/ml (about 73 µM) in a buffer composed of 50 mM Tris-HCl, 1 mM EDTA, pH 8.2. Ac-PYY-PEG3-Cys-β-Ala-Biotin and antibody were mixed at a 2.5:1 molar ratio (Ac-PYY-PEG3-Cys-β-Ala-Biotin to antibody) and incubated for 60 min at RT and 350 rpm. The resulting complex was defined as monomeric IgG-like molecule via the occurrence of a single peak in a size exclusion chromatography (95% monomer). The resulting complex was further analyzed by SDS-PAGE and subsequent Western Blot analysis. 10 µg of the complex were mixed with 4× LDS sample buffer (Invitrogen) and incubated at 95° C. for 5 min. The sample was applied to a 4-12% Bis-Tris polyacrylamide-gel (NuPAGE, Invitrogen) which was run for 35 min at 200V and 120 mA. Molecules that were separated in the polyacrylamide-gel were transferred to a PVDF membrane (0.2 µm pore size, Invitrogen) for 40 min at 25V and 160 mA. The membrane was blocked in 1% (w/v) skim milk in 1× PBST (1× PBS+0.1% Tween20) for 1 h at RT. The membrane was washed 3× for 5 min in 1× PBST and subsequently incubated with a streptavidin-POD-conjugate (2900 U/ml, Roche) which was used in a 1:2000 dilution. Detection of streptavidin-POD bound to biotin on the membrane was carried out using Lumi-Light Western Blotting Substrate (Roche).

Exemplary Method for the Formation of Complexes of Biotinylated Polypeptides and Anti-Biotin Antibodies—Ac-PYY-PEG3-Cys-PEG2-Biotin/Chimeric Anti-Biotin Antibody Complex:

For the generation of non-covalent complexes of biotinylated-PYY-polypeptide containing a cysteinylated linker, 0.16 mg of Ac-PYY-PEG3-Cys-PEG2-Biotin were dissolved in 100% DMF to a concentration of 10 mg/ml. The antibody was used in a concentration of 10.7 mg/ml (about 73 µM) in a buffer composed of 50 mM Tris-HCl, 1 mM EDTA, pH 8.2. Ac-PYY-PEG3-Cys-PEG2-Biotin and antibody were mixed at a 2.5:1 molar ratio (Ac-PYY-PEG3-Cys-PEG2-Biotin to antibody) and incubated for 60 min at RT and 350 rpm. The resulting complex was defined as 63% monomeric IgG-like molecule and 37% dimeric soluble aggregates via size exclusion chromatography. The resulting complex was further analyzed by SDS-PAGE and subsequent Western Blot analysis. 10 µg of the complex were mixed with 4× LDS sample buffer (Invitrogen) and incubated at 95° C. for 5 min. The sample was applied to a 4-12% Bis-Tris polyacrylamide-gel (NuPAGE, Invitrogen) which was run for 35 min at 200V and 120 mA. Molecules that were separated in the polyacrylamide-gel were transferred to a PVDF membrane (0.2 µm pore size, Invitrogen) for 40 min at 25V and 160 mA. The membrane was blocked in 1% (w/v) skim milk in 1× PBST (1× PBS+0.1% Tween20) for 1 h at RT. The membrane was washed 3× for 5 min in 1× PBST and subsequently incubated with a streptavidin-POD-conjugate (2900 U/ml, Roche) which was used in a 1:2000 dilution. Detection of streptavidin-POD bound to biotin on the membrane was carried out using Lumi-Light Western Blotting Substrate (Roche).

Generation of Defined Covalent Conjugates of Haptenylated Dyes and Polypeptides with an Anti-Hapten Antibody VH53C in the Absence of Redox Agents For the generation of covalent anti-biotin antibody/biotinylated polypeptide or biotinylated dye disulfide-linked conjugates it is necessary to (i) couple biotin via a suitable a reactive group (such as e.g. cysteine, maleimide) containing linkers to the polypeptide or dye that allows the polypeptide to be exposed above the antibody surface and hence to retain its activity, and (ii) generate covalent site specific conjugates of the biotinylated polypeptides with the anti-biotin antibody with a cysteine mutation (=antibody VH52bC/VH53C) in which the biological activity of the polypeptide is retained, and (iii) to carry out the reaction in the absence of a reducing agent in order to avoid the reduction of antibody inter-chain disulfide bridges.

General Method:

The generation of conjugates of anti-biotin antibodies with biotinylated compounds shall result in conjugates with defined stoichiometry and it shall be assured that the compound in these conjugates retains its activity. For the generation of conjugates of biotinylated compounds with the anti-biotin antibody the biotinylated compound was dissolved in 100% DMF to a final concentration of 10 mg/ml. The anti-biotin antibody VH52bC/VH53C was brought to a concentration of 10 mg/ml in 50 mM Tris-HCl, 1 mM EDTA, pH=8.2. Biotinylated compound and anti-biotin antibody VH52bC/VH53C were mixed in a 2.5:1 molar ratio (compound to antibody) by pipetting up and down and incubated for 60 minutes at RT and 350 rpm.

A polypeptide conjugated to biotin via a cysteine containing linker is termed biotin-Cys-polypeptide or polypeptide-Cys-biotin in the following. The polypeptide may either have a free N-terminus or a capped N-terminus e.g. with an acetyl-group (Ac-polypeptide-Cys-biotin) or a PEG-residue (PEG-polypeptide-Cys-biotin).

A fluorescent dye conjugated to biotin via a cysteine containing linker is termed dye-Cys-biotin or biotin-Cys-dye in the following.

Exemplary Method for the Formation of Conjugates of Biotinylated Fluorescent Dyes and Anti-Biotin Antibodies—Biotin-Ser-Cy5/Humanized Anti-Biotin Antibody:

For the generation of complexes of biotin-derivatized-Cy5 (Biotin-Ser-Cy5) containing a serine residue within the linker, 0.61 mg of Biotin-Ser-Cy5 were dissolved in 20 mM histidine, 140 mM NaCl, pH 6.0 to a concentration of 10 mg/ml. 18.5 mg of the humanized anti-biotin antibody was used in a concentration of 10 mg/ml (about 69 µM) in a buffer composed of 50 mM Tris-HCl, 1 mM EDTA, pH 8.2. Biotin-Ser-Cy5 and antibody were mixed at a 2.5:1 molar ratio (Biotin-Ser-Cy5 to antibody) and incubated for 60 min at RT, shaken at 350 rpm. The sample was then subjected to size exclusion chromatography using Superdex 200 16/60 high load prep grade column (GE Healthcare) with a flow rate of 1.5 ml/min and 20 mM histidine, 140 mM NaCl, pH 6.0 as the mobile phase. Peak fractions were collected and analyzed by SDS-PAGE for purity. The dye to antibody ratio was calculated by (1) measuring the absorbance of the samples at the wavelength 280 nm (protein) and 650 nm (Cy5); (2) using the formula: $A_{650}$ of labeled protein/c (Cy5)*protein concentration (M)=moles dye per mole protein, where $\epsilon$(Cy5)=250000 $M^{-1}$ $cm^{-1}$, $A_{650}$ of the complex=47.0 and the protein concentration is 86.67 µM. The resulting ratio of dye to antibody molecule was 2.17 which suggests that all antibody paratopes are saturated with Biotin-Cy5 molecules.

Exemplary Method for the Formation of Conjugates of Biotinylated Fluorescent Dyes and Anti-Biotin Antibodies—Biotin-Cys-Cy5/Chimeric Anti-Biotin Antibody VH53C:

For the generation of conjugates of biotin-derivatized-Cy5 containing a cysteinylated linker, 0.16 mg of Biotin-Cys-Cy5 were dissolved in 100% DMF to a concentration of 10 mg/ml. 1 mg of the anti-biotin antibody VH53C was used in a concentration of 9.7 mg/ml (about 68 µM) in a buffer composed of 50 mM Tris-HCl, 1 mM EDTA, pH 8.2. Biotin-Cys-Cy5 and antibody were mixed at a 2.5:1 molar ratio (Ac-Biotin-Cys-Cy5 to antibody) and incubated for 60 min at RT, shaken at 350 rpm. The resulting conjugate was analyzed by SDS-PAGE as described in Example 7. Detection of fluorescence was carried out as described in Example 7.

Exemplary Method for the Formation of Conjugates of Biotinylated Fluorescent Dyes and Anti-Biotin Antibodies—Biotin-Cys-Cy5/Humanized Anti-Biotin Antibody VH53C:

For the generation of conjugates of biotin-derivatized-Cy5 containing a cysteinylated linker, 0.16 mg of Biotin-Cys-Cy5 were dissolved in 100% DMF to a concentration of 10 mg/ml. 1 mg of the humanized anti-biotin antibody VH53C was used in a concentration of 7.4 mg/ml (about 51 µM) in a buffer composed of 50 mM Tris-HCl, 1 mM EDTA, pH 8.2. Biotin-Cys-Cy5 and antibody were mixed at a 2.5:1 molar ratio (Ac-Biotin-Cys-Cy5 to antibody) and incubated for 60 min at RT, shaken at 350 rpm. The resulting conjugate was analyzed by SDS-PAGE as described in Example 7. Detection of fluorescence was carried out as described in Example 7.

Exemplary Method for the Formation of Conjugates of Biotinylated Polypeptides and Anti-Biotin Antibodies—Ac-PYY(PEG3-Cys-βAla-Biotin)/Chimeric Anti-Biotin Antibody VH53C:

For the generation of conjugates of biotin-derivatized-PYY-polypeptide containing a cysteinylated linker, 0.19 mg of Ac-PYY(PEG3-Cys-βAla-Biotin) were dissolved in 100% DMF to a concentration of 10 mg/ml. 1 mg of the chimeric anti-biotin antibody VH53C was used in a concentration of 9.7 mg/ml (about 67 µM) in a buffer composed of 50 mM Tris-HCl, 1 mM EDTA, pH 8.2. Ac-PYY(PEG3-Cys-βAla-Biotin) and antibody were mixed at a 2.5:1 molar ratio (Ac-PYY(PEG3-Cys-βAla-Biotin) to antibody) and incubated for 60 min at RT, shaken at 350 rpm. The resulting conjugate was analyzed by mass spectrometry. 87.7% of the detected species was identified as antibody coupled to 2 peptide molecules, 12.3% was identified as antibody coupled to 1 peptide molecule.

Exemplary Method for the Formation of Conjugates of Biotinylated Polypeptides and Anti-Biotin Antibodies—Ac-PYY(PEG3-Cys-PEG2-Biotin)/Chimeric Anti-Biotin Antibody VH53C:

For the generation of conjugates of biotin-derivatized-PYY-polypeptide containing a cysteinylated linker, 0.16 mg of Ac-PYY(PEG3-Cys-PEG2-Biotin) were dissolved in 100% DMF to a concentration of 10 mg/ml. 1 mg of the chimeric anti-biotin antibody VH53C was used in a concentration of 9.9 mg/ml (about 68 µM) in a buffer composed of 50 mM Tris-HCl, 1 mM EDTA, pH 8.2. Ac-PYY(PEG3-Cys-PEG2-Biotin) and antibody were mixed at a 2.5:1 molar ratio (Ac-PYY(PEG3-Cys-PEG2-Biotin) to antibody) and incubated for 60 min at RT, shaken at 350 rpm. The resulting conjugate was analyzed by mass spectrometry. 100% of the detected species was identified as antibody coupled to 2 peptide molecules.

Exemplary Method for the Formation of Conjugates of Biotinylated Polypeptides and Anti-Biotin Antibodies—Ac-PYY(PEG3-Cys-βAla-Biotin)/Humanized Anti-Biotin Antibody VH53C:

For the generation of conjugates of biotin-derivatized-PYY-polypeptide containing a cysteinylated linker, 0.06 mg of Ac-PYY(PEG3-Cys-βAla-Biotin) were dissolved in 100% DMF to a concentration of 10 mg/ml. 0.8 mg of the humanized anti-biotin antibody VH53C was used in a concentration of 9 mg/ml (about 62 µM) in a buffer composed of 50 mM Tris-HCl, 1 mM EDTA, pH 8.2. Ac-PYY(PEG3-Cys-βAla-Biotin) and antibody were mixed at a 2.5:1 molar ratio (Ac-PYY(PEG3-Cys-βAla-Biotin) to antibody) and incubated for 60 min at RT, shaken at 350 rpm. The resulting conjugate was analyzed by mass spectrometry. 62.2% of the detected species was identified as antibody coupled to 2 peptide molecules, 33.9% was identified as antibody coupled to 1 peptide molecule and 3.9% was identified as uncoupled antibody.

Exemplary Method for the Formation of Conjugates of Biotinylated Polypeptides and Anti-Biotin Antibodies—Ac-PYY(PEG3-Cys-PEG2-Biotin)/Humanized Anti-Biotin Antibody VH53C For the generation of conjugates of biotin-derivatized-PYY-polypeptide containing a cysteinylated linker, 0.08 mg of Ac-PYY(PEG3-Cys-PEG2-Biotin) were dissolved in 100% DMF to a concentration of 10 mg/ml. 0.8 mg of the humanized anti-biotin antibody VH53C was used in a concentration of 9 mg/ml (about 62 µM) in a buffer composed of 50 mM Tris-HCl, 1 mM EDTA, pH 8.2. Ac-PYY(PEG3-Cys-PEG2-Biotin) and antibody were mixed at a 2.5:1 molar ratio (Ac-PYY(PEG3-Cys-PEG2-Biotin) to antibody) and incubated for 60 min at RT, shaken at 350 rpm. The resulting conjugate was analyzed by mass spectrometry. 71.4% of the detected species was identified as antibody coupled to 2 peptide molecules, 26% was identified as antibody coupled to 1 peptide molecule and 2.5% was identified as uncoupled antibody.

Example 7

Detection Methods
SDS-Gel Electrophoresis:

For SDS gel electrophoresis, 4× LDS sample buffer (Invitrogen) was added to the samples. For each sample also a reduced version was prepared by adding 10× NuPAGE sample reducing agent (Invitrogen). All samples were incubated at 70° C. for 5 min before electrophoresis on a 4-12% Bis-Tris polyacrylamide gel (NuPAGE, Invitrogen) with 1× MOPS buffer (Invitrogen).

Fluorescence Detection:

Cy5-related fluorescence in the gel was detected with a Lumilmager F1 device (Roche) at an excitation wavelength of 645 nm. After detection of fluorescence, the gel was stained with SimplyBlue SafeStain (Invitrogen).

Example 8

Serum Stability

Serum stability of complexes of biotinylated Cy5 with humanized anti-biotin antibody in comparison to covalent conjugates of biotinylated Cy5 with humanized anti-biotin antibody VH53C.

The objective of the described peptide modification technology is to improve the therapeutic applicability of peptides. Major bottlenecks for therapeutic application of peptides are currently limited stability in vivo and/or short serum half-life and fast clearance. The PK parameters of antibody conjugates of fluorophores were determined in vivo and compare with the PK of non-covalent antibody-fluorophore complexes. Therefore, (i) the anti-biotin antibody VH53C was covalently conjugated to the biotinylated fluorophore Biot-Cys-Cy5, (ii) a non-covalent complex of the anti-biotin antibody with biotinylated fluorophore Biot-Cy5 was generated, (iii) the covalently conjugated and the non-covalently complexed compounds were applied to animals and (iv) the serum concentrations of the compounds over time in these animals was analyzed.

Experimental Procedure:

To analyze the influence on PK parameters of antibody-complexation of a small fluorescent substrate, 13 nmol of Cy5-Biotin/humanized anti-biotin antibody disulfide-linked conjugate or of the corresponding antibody non-covalently complexed compound in 20 mM histidine/140 mM NaCl, pH 6.0 are applied to six female mice (strain NRMI) for each substance. About 0.1 ml blood samples are collected after the following time points: 0.08 h, 8 h and 48 h for Mouse 1 and 2 and 0.08 h, 24 h and 48 h for Mouse 3 and 4 and 0.08 h, 36 h and 48 h for Mouse 5 and 6. Serum samples of at least 40 µl are obtained after 1 h at RT by centrifugation (9,300×g, 3 min, 4° C.). Serum samples are stored at −80° C.

To determine the amount of compound in the serum at the given time points the fluorescent properties of Cy5 are used: Cy5 related fluorescence in serum samples are measured in 120 µl quartz cuvettes at room temperature using a Cary Eclipse Fluorescence Spectrophotometer (Varian). Excitation wavelength is 649 nm, Emission is measured at 670 nm. Serum samples are diluted in 1× PBS to reach an appropriate range of Emission intensity. Blood serum of an untreated mouse in the same dilution in 1× PBS as the respective sample is used as a blank probe.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

Example 9

Figure 2:
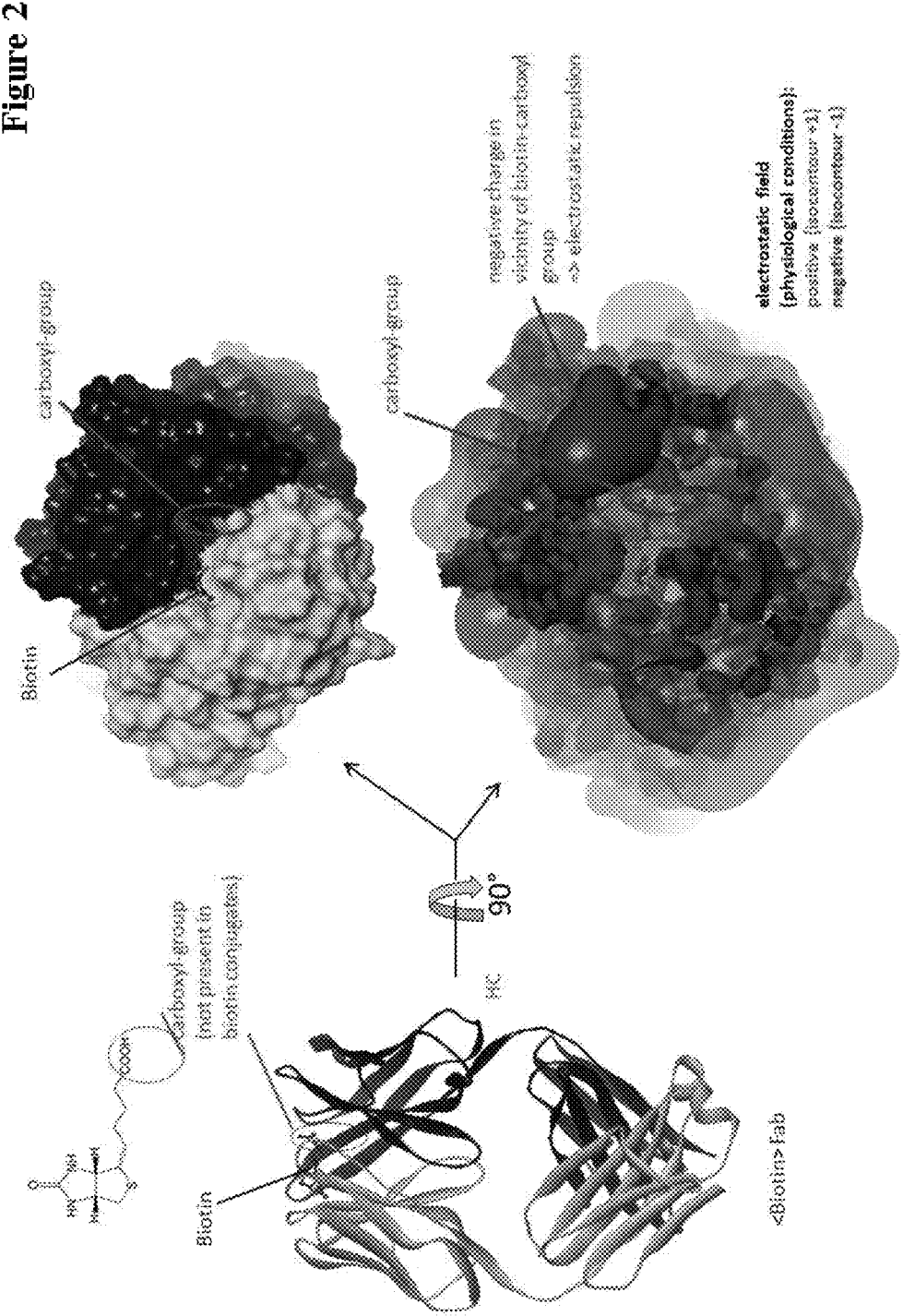
FIG. 2 The protein structure of murine anti-Biotin antibody-Fab-fragment was determined in complex with biocytinamid: the complexed hapten is positioned in close proximity to a negatively charged cluster of amino acids; biotin which—as hapten—is derivatized for payload coupling at its carboxyl group binds with good efficacy as there is no charge repulsion at this position (due to the lack of the COOH group); in contrast, free (normal) biotin would be in close proximity to this negative charge cluster, and hence becomes repulsed.

X-Ray Structure Determination of Murine Anti-Biotin Antibody-Fab-Fragments in Complex with Biocytinamid The protein structure of murine anti-Biotin antibody Fab-fragment was determined in complex with biocytinamid. Therefore, crystals of the Fab-fragment were grown in 0.8 M Succinic Acid, followed by charging of the antibody crystals with Biocytidinamide (diluted to 10 mM working concentration in crystallization solution, applied to the crystals in the crystallization droplet). Crystals were washed three times with 2 µl of 10 mM Biocytidinamide solution and were finally incubated for 16 hrs. with Biocytidinamide at 21° C., harvested with 15% Glycerol as cryoprotectant and flash frozen in liquid nitrogen. Processed diffraction images yielded a protein structure at 2.5 Å resolution. The structure and charge composition of the biotin-binding variable region is shown in FIG. 2: Biotin binds into a surface pocket which is flanked by charged regions that composed of amino acids from the CDR regions. The complexed hapten is positioned in close proximity to a negatively charged cluster of amino acids. Biotin which—as hapten—is derivatized for payload coupling at its carboxyl group binds with good efficacy as there is no charge repulsion at this position (due to the lack of the COOH group). In contrast, free (normal) biotin cannot bind efficient to the antibody because its carboxyl group would be in close proximity to this negative charge cluster, and hence becomes repulsed.

What is claimed is:

1. An anti-biotin antibody, wherein the antibody comprises (a) a heavy chain hyper variable region 1 (HVR-H1) comprising the amino acid sequence of SEQ ID NO: 09; (b) a HVR-H2 comprising the amino acid sequence of SEQ ID NO: 10; (c) a HVR-H3 comprising the amino acid sequence of SEQ ID NO: 11; (d) a light chain hyper variable region 1 (HVR-L1) comprising the amino acid sequence of SEQ ID NO: 13; (e) a HVR-L2 comprising the amino acid sequence of SEQ ID NO: 14; (f) a HVR-L3 comprising the amino acid sequence of SEQ ID NO: 15.

2. The antibody of claim 1 comprising at position 24 of the heavy chain variable domain numbered according to Kabat the amino acid residue serine or comprising at position 73 of the heavy chain variable domain numbered according to Kabat the amino acid residue threonine.

3. The antibody of claim 1 comprising at position 60 of the heavy chain variable domain numbered according to Kabat the amino acid residue alanine and at position 61 of the heavy chain variable domain numbered according to Kabat the amino acid residue glutamine.

4. The antibody of claim 1 comprising
(a) a variable heavy chain domain (VH) sequence having at least 95% sequence identity to the amino acid sequence of SEQ ID NO: 12;
(b) a variable light chain domain (VL) sequence having at least 95% sequence identity to the amino acid sequence of SEQ ID NO: 16; or
(c) a VH sequence as in (a) and a VL sequence as in (b), wherein the amino acid residue at position 24 of the heavy chain variable domain numbered according to Kabat is serine or the amino acid residue at position 73 of the heavy chain variable domain numbered according to Kabat is threonine.

5. The antibody of claim 2, comprising a VH sequence of SEQ ID NO: 12.

6. The antibody of claim 2, comprising a VL sequence of SEQ ID NO: 16.

7. An antibody comprising a VH sequence of SEQ ID NO: 12 and a VL sequence of SEQ ID NO: 16.

8. The antibody of claim 1, wherein the antibody is a full length IgG1 antibody or a full length IgG4 antibody.

9. The antibody of claim 1, wherein the antibody is a monoclonal antibody.

10. The antibody of claim 1, wherein the antibody is an antibody fragment that binds biotin.

11. A pharmaceutical formulation comprising the antibody of claim 1 and a pharmaceutically acceptable carrier.

12. The antibody of claim 1, wherein the antibody is humanized.

13. The antibody of claim 1 comprising at position 24 of the heavy chain variable domain numbered according to Kabat the amino acid residue serine and comprising at position 73 of the heavy chain variable domain numbered according to Kabat the amino acid residue threonine.

14. The antibody of claim 1, wherein the antibody is conjugated to one or more cytotoxic agents in an immunoconjugate.

15. The antibody of claim 1, wherein the antibody further comprises a label.

16. A complex comprising the antibody of claim 1 and a biotinylated compound.

17. A method of delivering a biotinylated compound in an individual to the surface of a cell comprising administering to the individual an effective amount of the complex of claim 16.

18. A multispecific antibody comprising (a) a heavy chain hyper variable region 1 (HVR-H1) comprising the amino acid sequence of SEQ ID NO: 09; (b) a HVR-H2 comprising the amino acid sequence of SEQ ID NO: 10; (c) a HVR-H3 comprising the amino acid sequence of SEQ ID NO: 11; (d) a HVR-L1 comprising the amino acid sequence of SEQ ID NO: 13: (e) a HVR-L2 comprising the amino acid sequence of SEQ ID NO: 14; (f) a HVR-L3 comprising the amino acid sequence of SEQ ID NO: 15.

19. The multispecific antibody of claim 18, wherein the antibody further binds to a cell surface molecule.

20. A complex comprising the antibody of claim 18 and a biotinylated compound.

* * * * *